(12) United States Patent
Malherbe et al.

(10) Patent No.: US 7,576,217 B2
(45) Date of Patent: Aug. 18, 2009

(54) QUINOLINES AS ALLOSTERIC ENHANCERS OF THE GABA$_B$ RECEPTORS

(75) Inventors: Parichehr Malherbe, Muttenz (CH); Raffaello Masciadri, Basel (CH); Roger David Norcross, Olsberg (CH); Hasane Ratni, Habsheim (FR); Andrew William Thomas, Birsfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 536 days.

(21) Appl. No.: 11/259,860

(22) Filed: Oct. 27, 2005

(65) Prior Publication Data

US 2006/0094754 A1 May 4, 2006

(30) Foreign Application Priority Data

Nov. 1, 2004 (EP) .................. 04105429

(51) Int. Cl.
*C07D 215/38* (2006.01)
(52) U.S. Cl. ..................... 546/159; 546/163
(58) Field of Classification Search .......... 546/159, 546/163
See application file for complete search history.

(56) References Cited

U.S. PATENT DOCUMENTS 5,641,788 A * 6/1997 Sohda et al. ............. 514/312
6,313,146 B1 11/2001 Van Wagenen et al.

FOREIGN PATENT DOCUMENTS

WO    WO 03/090731    11/2003
WO    WO 2004/043930   5/2004

OTHER PUBLICATIONS

Sinsky, CA 102:45748 abstract only of J of Het Chem, vol. 21(3), pp. 759-768, 1984.*
Vigante, CA 117:171184, abstract only of Khimiya Geterotsiklicheskikh Soedinenii, vol. 12, pp. 1680-1686, 1991.*
Walser, CA 84:179997, abstract only of J of Het Chem, vol. 13(1), pp. 131-133, 1976.*
Arcadi, CA 138:401582, abstract only of Synlett, vol. 2, pp. 203-206, 2006.*
Ubeda, CA 131:228671, abstract only of Synthesis, vol. 8, pp. 1335-1340, 1999.*
Yadav, Synlett, vol. 6, pp. 963-966, 2004.*
Vacher et al., Curr. Drug Targets, CNS Neurol. Disord. 2, pp. 248-259, 2003.
Bettler, et al., Physiol Rev. 84, pp. 835-867, 2004.
Kaupmann et al., Nature, 386, pp. 239-246, 1997.
Kaupmann et al., Nature, 396, pp. 683-687, 1998.
Pin et al., Pharmaco. Ther. 98, pp. 325-354, 2003.
Havlickova et al., Mol. Pharmacol. 62, pp. 343-350, 2002.
Kniazeff et al., J. Neurosci., 22, pp. 7352-7361, 2002.
Schuler et al., Neuron, 31, pp. 47-58, 2001.
Peters et al., Neurogenetics, 2, pp. 47-54, 1998.
Mondabon et al., Am. J. Med. Genet 122B/1, p. 134, 2003.
Gassmann et al., J Neurosci. 24, pp. 6086-6097, 2004.
Misgeld et al., Prog. Neurobiol. 46, pp. 423-462, 1995.
Enna et al., Life Sci, 62, pp. 1525-1530, 1998.
McCarson et al., Neuropharmacology, 38, pp. 1767-1773, 1999.
Brebner et al., Neuropharmacology, 38, pp. 1797-1804, 1999.
Paterson et al., Psychopharmacology, 172, pp. 179-186, 2004.
Breslow et al., Am. J. Psychiatry, 146, pp. 353-356, 1989.
Drake et al., Ann. Pharmacother. 37., pp. 1177-1181, 2003.
Bortolato et al., Psychopharmacology, 171, pp. 322-330, 2004.
Urwyler et al., Mol. Pharmacol., 60, pp. 963-971, 2001.
Pin et al., Mol. Pharmacol., 60, pp. 881-884, 2001.
Binet et al., J Biol Chem., 279, pp. 29085-29091, 2004.
Mombereau et al., Neuropsychopharmacology, 29, pp. 1050-1062, 2004.
Urwyler et al., J. Pharmacol. Exp. Ther., 307, pp. 322-330, 2003.
Cryan et al., J Pharmacol Exp Ther., 310, pp. 952-963, 2004.
Smith et al., Psychopharmacology, 173, pp. 105-111, 2004.
Fuson, R.C., et al., J. Am. Chem. Soc., vol. 79, pp. 3477-3480 (1957) XP002367350.
Walser, A., et al., J. Heterocycl. Chem., vol. 13, pp. 131-133 (1976) XP002367351.
Sinsky, M.D., et al., J. heterocycl. Chem., vol. 21, pp. 759-768 (1984) XP002367352.
Arcadi, A., et al., Synlett., pp. 203-206 (2003) XP002367353.
Sato, Susumu, et al., Chemical Abstracts Service, XP002367441 & JP 2002 371078 A2.
Chemical Abstracts, XP002367442, Publ. Date Apr. 25, 2003.
Chemical Abstracts, XP002367443, Publ. Date Sep. 27, 2004.
Urwyler, S., et al., Molecular Pharmacology, vol. 60, No. 5, Nov. 2001, pp. 963-971 XP001153169.
Urwyler, S., et al., American Chemical Society, vol. 225, No. ½, Mar. 2003, p. MED1317 XP009029992.

* cited by examiner

*Primary Examiner*—D. Margaret Seaman
(74) *Attorney, Agent, or Firm*—George W. Johnston; Patricia S. Rocha-Tramaloni; Kimberly J. Prior

(57) ABSTRACT

The present invention relates to compounds of formula I

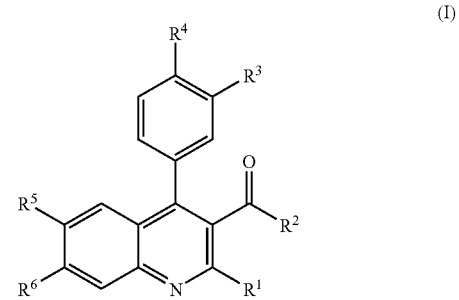

(I)

wherein $R^1$ to $R^6$ are as described herein, which compounds are active at the GABA$_B$ receptor and can be used for the preparation of medicaments useful in the treatment of CNS disorders comprising anxiety and depression.

24 Claims, No Drawings

QUINOLINES AS ALLOSTERIC ENHANCERS OF THE GABA$_B$ RECEPTORS

PRIORITY TO RELATED APPLICATIONS

This application claims the benefit of European Application No. 04105429.7, filed Nov. 1, 2004, which is hereby incorporated by reference in its entirety.

BACKGROUND OF THE INVENTION

γ-Aminobutyric acid (GABA), the most abundant inhibitory neurotransmitter, activates both ionotropic GABA$_{A/C}$ and metabotropic GABA$_B$ receptors (Hill and Bowery, Nature, 290, 149-152, 1981). GABA$_B$ receptors that are present in most regions of the mammalian brain on presynaptic terminals and postsynaptic neurons are involved in the fine-tuning of inhibitory synaptic transmission. Presynaptic GABA$_B$ receptors through modulation of high-voltage activated Ca$^{2+}$ channels (P/Q- and N-type) inhibit the release of many neurotransmitters. Postsynaptic GABA$_B$ receptors activates G-protein coupled inwardly rectifying K+ (GIRK) channel and regulates adenylyl cyclase (Billinton et al., Trends Neurosci., 24, 277-282, 2001; Bowery et al., Pharmacol. Rev. 54, 247-264, 2002). Because the GABA$_B$ receptors are strategically located to modulate the activity of various neurotransmitter systems, GABA$_B$ receptor ligands hence could have potential therapeutics in the treatment of anxiety, depression, epilepsy, schizophrenia and cognitive disorders (Vacher and Bettler, Curr. Drug Target, CNS Neurol. Disord. 2, 248-259, 2003; Bettler et al., Physiol Rev. 84, 835-867, 2004).

Native GABA$_B$ receptors are heteromeric structures composed of two types of subunits, GABA$_B$R1 and GABA$_B$R2 subunits (Kaupmann et al., Nature, 386, 239-246, 1997 and Nature, 396, 683-687, 1998). The structure of GABA$_B$R1 and R2 show that they belong to a family of G-protein coupled receptors (GPCRs) called family 3. Other members of the family 3 GPCRs include the metabotropic glutamate (mGlu1-8), Calcium-sensing, vomeronasal, pheromone and putative taste receptors (Pin et al., Pharmaco. Ther. 98, 325-354, 2003). The family 3 receptors (including GABA$_B$ receptors) are characterized by two distinctly separated topological domains: an exceptionally long extracellular amino-terminal domain (ATD, 500-600 amino acids), which contains a venus flytrap module for the agonist binding (orthosteric site) (Galvez et al., J. Biol. Chem., 275, 41166-41174, 2000) and the 7TM helical segments plus intracellular carboxyl-terminal domain that is involved in receptor activation and G-protein coupling. The mechanism of receptor activation by agonist in GABA$_B$R1R2 heterodimer is unique among the GPCRs. In the heteromer, only GABA$_B$R1 subunit binds to GABA, while the GABA$_B$R2 is responsible for coupling and activation of G-protein (Havlickova et al., Mol. Pharmacol. 62, 343-350, 2002; Kniazeff et al., J. Neurosci., 22, 7352-7361, 2002).

Schuler et al., Neuron, 31, 47-58, 2001 have demonstrated that the GABA$_B$R1 knock-out (KO) mice exhibit spontaneous seizures and hyperalgesia. These KO mice have lost all the biochemical and electrophysiological GABA$_B$ responses. Interestingly, the GABA$_B$R1 KO mice were more anxious in two anxiety paradigm, namely the light-dark box (decreased time in light) and staircase tests (decreased rears and steps climbed). They showed a clear impairment of passive avoidance performance model indicating impaired memory processes. The GABA$_B$R1 KO also displayed increased hyperlocomotion and hyperactivity in new environment. The GABA$_B$R1 gene is mapped to chromosome 6p21.3, which is within the HLA class I, a region with linkage for schizophrenia, epilepsy and dyslexia (Peters et al., Neurogenetics, 2, 47-54, 1998). Mondabon et al., Am. J. Med. Genet 122B/1, 134, 2003 have reported about a weak association of the Ala20Val polymorphism of GABA$_B$R1 gene with schizophrenia. Moreover, Gassmann et al., J Neurosci. 24, 6086-6097, 2004 has shown that GABA$_B$R2KO mice suffer from spontaneous seizures, hyperalgesia, hyperlocomotor activity and severe memory impairment, comparable to GABA$_B$R1KO mice. Therefore, heteromeric GABA$_B$ R1R2 receptors are responsible for these phenotypes.

Baclofen (Lioresal®, β-chlorophenyl GABA), a selective GABA$_B$ receptor agonist with EC$_{50}$=210 nM at native receptor, is the only ligand, which has been used since 1972 in clinical study for the treatment of spasticity and skeletal muscle rigidity in patients following spinal cord injury, multiple sclerosis, amyotrophic lateral sclerosis, cerebral palsy. Most of the preclinical and clinical studies conducted with baclofen and GABA$_B$ receptor agonists were for the treatment of neuropathic pain and craving associated with cocaine and nicotine (Misgeld et al., Prog. Neurobiol. 46, 423-462, 1995; Enna et al., Life Sci, 62, 1525-1530, 1998; McCarson and Enna, Neuropharmacology, 38, 1767-1773, 1999; Brebner et al., Neuropharmacology, 38, 1797-1804, 1999; Paterson et al., Psychopharmacology, 172, 179-186, 2003). In panic disorder patients, Baclofen was shown to be significantly effective in reducing the number of panic attacks and symptoms of anxiety as assessed with the Hamilton anxiety scale, Zung anxiety scale and Katz-R nervousness subscale (Breslow et al., Am. J. Psychiatry, 146, 353-356, 1989). In a study with a small group of veterans with chronic, combat-related post-traumatic stress disorder (PTSD), baclofen was found to be an effective and well-tolerated treatment. It resulted in significant improvements in the overall symptoms of PTSD, most notably the avoidance, emotional numbing and hyperarousal symptoms and also in reduced accompanying anxiety and depression (Drake et al., Ann. Pharmacother. 37, 1177-1181, 2003). In preclinical study, baclofen was able to reverse the reduction in prepulse inhibition (PPI) of the acoustic startle response induced by dizocilpine, but not by apomorphine in rat PPI model of psychosis (Bortolato et al., Psychopharmacology, 171, 322-330, 2004). Therefore, GABA$_B$ receptor agonist has a potential in the pharmacological therapy of psychotic disorders. Unfortunately, Baclofen has a number of side-effects including the poor blood-brain-barrier penetration, very short duration of action and narrow therapeutic window (muscle relaxation, sedation and tolerance) that limit its utility.

Urwyler et al., Mol. Pharmacol., 60, 963-971, 2001 have reported on a novel class of GABA$_B$ receptor ligands, called positive allosteric modulators, CGP7930 [2,6-di-tert-butyl-4-(3-hydroxy-2,2-dimethyl-propyl)-phenol] and its aldehyde analogue CGP13501. These ligands have no effect on their own at GABA$_B$ receptors, but in concert with endogenous GABA, they increase both the potency and maximal efficacy of GABA at the GABA$_B$R1R2 (Pin et al., Mol. Pharmacol., 60, 881-884, 2001). Interestingly, recent study with CGP7930 (Binet et al., J Biol. Chem., 279, 29085-29091, 2004) has shown that this positive modulator activates directly the seven transmembrane domains (7TMD) of GABA$_B$R2 subunit. Mombereau et al., Neuropsychopharmacology, 1-13, 2004 have recently reported on the anxiolytic effects of acute and chronic treatment with the GABA$_B$ receptor positive modulator, GS39783 (N,N_-dicyclopentyl-2-methylsulfanyl-5-nitro-pyrimidine-4,6-diamine) (Urwyler et al., J. Pharmacol. Exp. Ther., 307, 322-330, 2003) in the light-dark box and elevated zero maze test models of anxiety. No tolerance after chronic treatment (21 days) with GS39783

(10 mg/kg, P.O., once daily) was observed. Because the GABA$_B$ enhancers have no effect on receptor activity in the absence of GABA, but do enhance allosterically the affinity of the GABA$_B$ receptor for the endogenous GABA, it is expected that these ligands should have an improved side effect profile as compared to baclofen. Indeed, GS39783 at 0.1-200 mg/kg, PO had no effect on spontaneous locomotor activity, rotarod, body temperature and traction test in comparison to baclofen, which showed these side effects at 2.5-15 mg/kg, PO. GS39783 did not have any effect on cognition performance as assessed by passive avoidance behavioral test in mice and rats. Furthermore, GS39783 exhibited anxiolytic-like effects in the elevated plus maze (rat), elevated zero maze (mice and rats), and the stress-induced hyperthermia (mice) test paradigms. Therefore, GS39783 represents a novel anxiolytic without side-effects associated with baclofen or benzodiazepines (Cryan et al., *J Pharmacol Exp Ther.*, 310, 952-963, 2004). The preclinical investigation with the CGP7930 and GS39783 has shown that both compounds were effective at deceasing cocaine self-administration in rats (Smith et al., *Psychopharmacology*, 173, 105-111, 2004). The positive modulator, CGP7930 has also been preclinically studied for the treatment of Gastro-Esophageal Reflux Disease (GERD) and was found to be effective (WO 03/090731, Use of GABA$_B$ receptor positive modulators in gastro-intestinal disorders).

Positive allosteric modulators have been reported for other family 3 GPCRs including mGlu1 receptor (Knoflach et al., *Proc. Natl. Acad. Sci., USA*, 98, 13402-13407, 2001; Wichmann et al., *Farmaco*, 57, 989-992, 2002), Calcium-sensing receptor (NPS R-467 and NPS R-568) (Hammerland et al., *Mol. Pharmacol.*, 53, 1083-1088, 1998) (U.S. Pat. No. 6,313, 146), mGlu2 receptor [LY487379, N-(4-(2-methoxyphenoxy)-phenyl-N-(2,2,2-trifluoroethylsulfonyl)-pyrid-3-ylmethylamine and its analogs] (WO 01/56990, Potentiators of glutamate receptors) and mGlu5 receptor (CPPHA, N-{4-chloro-2-[(1,3-dioxo-1,3-dihydro-2H-isoindol-2-yl)methyl] phenyl}-2-hydroxybenzamide) (O'Brien et al., *J. Pharmaco. Exp. Ther.*, 27, Jan. 27, 2004). Interestingly, it has been demonstrated that these positive modulators bind to a novel allosteric site located within the 7TMD region, thereby enhancing the agonist affinity by stabilizing the active state of the 7TMD region (Knoflach et al., *Proc. Natl. Acad. Sci., USA* 98, 13402-13407, 2001; Schaffhauser et al., *Mol. Pharmacol.*, 64, 798-810, 2003). Moreover, the NPS R-467, NPS R-568 (Tecalcet) and related compounds represent the first positive allosteric modulators that entered the clinical trails due to their allosteric mode of action.

SUMMARY OF THE INVENTION

The present invention provides compounds of formula I

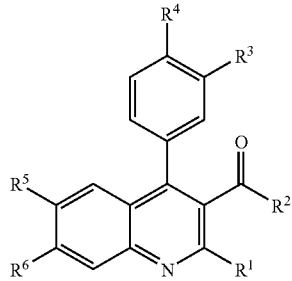

(I)

wherein
R$^1$ is hydrogen, C$_1$-C$_7$ alkyl, C$_1$-C$_7$ haloalkyl, di(C$_1$-C$_7$)alkylamino, C$_3$-C$_8$ cycloalkyl, or a 5 or 6 membered heterocycloalkyl;

R$^2$ is C$_1$-C$_7$ alkyl, aryl, C$_1$-C$_7$ alkoxy(C$_1$-C$_7$)alkyl, C$_1$-C$_7$ haloalkyl or C$_3$-C$_8$ cycloalkyl;

R$^3$ and R$^4$ are each independently hydrogen, halo, hydroxy, C$_1$-C$_7$ alkoxy, C$_1$-C$_7$ haloalkoxy, di(C$_1$-C$_7$)alkylamino, C$_1$-C$_7$ alkylsulfonyl, or a 5 or 6 membered heterocycloalkyl;

R$^5$ is hydrogen, halo, C$_1$-C$_7$ alkyl, C$_1$-C$_7$ alkoxy, C$_1$-C$_7$ haloalkoxy, aryloxy, or —NR$^7$R$^8$ wherein R$^7$ and R$^8$ are each independently C$_1$-C$_7$ alkyl, or R$^7$ and R$^8$, together with the nitrogen atom to which they are attached, form or a 4 to 8 membered heterocycloalkyl group which is optionally substituted by one or more subsituent(s) selected from the group consisting of halo, C$_1$-C$_7$ alkyl, C$_1$-C$_7$ alkoxy, hydroxy, phenyl and di(C$_1$-C$_7$)alkylamino; and R$^6$ is hydrogen or together with R$^5$ forms a 5 or 6 membered heterocycloalkyl group which is optionally substituted by one or more halogen;

and pharmaceutically acceptable acid addition salts thereof, excluding the following compounds:
1-(6-Chloro-2-methyl-4-phenyl-quinolin-3-yl)-ethanone;
1-(6-Bromo-4-phenyl-2-piperidin-1-yl-quinolin-3-yl)-ethanone;
1-[4-(4-Chloro-phenyl)-2-methyl-quinolin-3-yl]-ethanone;
1-(6-Bromo-2-methyl-4-phenyl-quinolin-3-yl)-ethanone;
1-(2,6-Dimethyl-4-phenyl-quinolin-3-yl)-ethanone; and
1-(2-Methyl-4-phenyl-6-trifluoromethoxy-quinolin-3-yl)-ethanone.

The six compounds excluded from the scope for formula I are known from chemical libraries. Said six compounds were never disclosed in relation with GABA$_B$ receptors.

The compounds of formula I and their salts are distinguished by valuable therapeutic properties. The compounds are active on the GABA$_B$ receptor.

The invention also provides pharmaceutical compositions that comprise a therapeutically effective amount of a compound of formula I or a pharmaceutically acceptable acid addition salt thereof and a pharmaceutically acceptable carrier.

The invention further provides a method for treating a disorder selected from anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders or gastro-intestinal disorders, which comprises administering a compound of formula I or a pharmaceutically acceptable acid addition salt thereof. The invention also provides a method for treating a disorder selected from anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders or gastro-intestinal disorders, which comprises administering a compound selected from the group consisting of:
1-(6-Chloro-2-methyl-4-phenyl-quinolin-3-yl)-ethanone;
1-(6-Bromo-4-phenyl-2-piperidin-1-yl-quinolin-3-yl)-ethanone;
1-[4-(4-Chloro-phenyl)-2-methyl-quinolin-3-yl]-ethanone;
1-(6-Bromo-2-methyl-4-phenyl-quinolin-3-yl)-ethanone;
1-(2,6-Dimethyl-4-phenyl-quinolin-3-yl)-ethanone; and
1-(2-Methyl-4-phenyl-6-trifluoromethoxy-quinolin-3-yl)-ethanone, or a pharmaceutically acceptable acid addition salt thereof.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "aryl" means a monovalent cyclic aromatic hydrocarbon moiety. Preferred aryls include, but are not limited to, optionally substituted phenyl or naphthyl, as well as those aryl groups specifically illustrated by the examples herein below. Examples of subisitutents for aryl groups are hydroxy, halo, $C_1$-$C_7$ alkyl, $C_1$-$C_7$ haloalkyl, $C_1$-$C_7$ alkoxy, $C_1$-$C_7$ haloalkoxy, $C_1$-$C_7$ alkoxyalkyl, $C_1$-$C_7$ alkylsulfonyl, di($C_1$-$C_7$)alkylamino or $C_3$-$C_8$ cycloalkyl.

"Aryloxy" denotes an aryl group wherein the aryl group is as defined above and the aryl group is connected via an oxygen atom. Prefered aryloxy is PhO—.

"$C_1$-$C_7$ alkyl" denotes a straight- or branched-carbon chain group containing from 1 to 7 carbon atoms, for example, methyl, ethyl, propyl, isopropyl, isobutyl, sec-butyl, tert-butyl, pentyl, n-hexyl as well as those groups specifically illustrated by the examples herein below.

"$C_1$-$C_7$ haloalkyl" denotes a $C_1$-$C_7$ alkyl group as defined above which is substituted by one or more halogen atoms. Examples of $C_1$-$C_7$ haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Prefered $C_1$-$C_7$ haloalkyl are difluoro- or trifluoro-methyl or ethyl.

"$C_1$-$C_7$ alkoxy" denotes an alkyl group is as defined above connected via an oxygen atom. Prefered alkoxy are MeO— and Et—O as well as those groups specifically illustrated by the examples herein below.

"$C_1$-$C_7$ haloalkoxy" denotes a $C_1$-$C_7$ alkoxy group as defined above which is substituted by one or more halogen. Examples of $C_1$-$C_7$ haloalkoxy include but are not limited to methoxy or ethoxy, substituted by one or more Cl, F, Br or I atom(s) as well as those groups specifically illustrated by the examples herein below. Prefered $C_1$-$C_7$ haloalkoxy are difluoro- or trifluoromethoxy or ethoxy.

"Halogen" or "halo" denotes chlorine, iodine, fluorine and bromine.

"$C_1$-$C_7$ alkoxyalkyl" denotes a $C_1$-$C_7$ alkyl group as defined herein above which is substituted by a $C_1$-$C_7$ alkoxy group as defined herein above.

"$C_1$-$C_7$ alkylsulfonyl" denotes a sulfonyl group which is substituted by a $C_1$-$C_7$ alkyl group as defined herein above. Examples of $C_1$-$C_7$ alkylsulfonyl include but are not limited to methylsulfonyl and ethylsulfonyl as well as those groups specifically illustrated by the examples herein below.

"di($C_1$-$C_7$)alkylamino" denotes an —$NR^7R^8$ group, wherein $R^7$ and $R^8$ are each independently a $C_1$-$C_7$ alkyl group as defined herein above. Examples of di($C_1$-$C_7$)alkylamino groups include but are not limited to di(methyl)amino, di(ethyl)amino, methylethylamino, as well as those groups specifically illustrated by the examples herein below.

"Hydroxy" denotes a —OH group.

"$C_3$-$C_8$ cycloalkyl" denotes a saturated carbon cyclic ring having 3 to 8 carbon atoms as ring members and includes but is not limited to cyclopropyl, cyclobutyl, cyclopentyl, cyclohexyl, cycloheptyl, as well as those groups specifically illustrated by the examples herein below.

"4 to 8 membered heterocycloalkyl" denote a saturated mono- or bi-cyclic ring comprising from 1 to 7 carbon atoms as ring members, the other remaining ring member atoms being selected from one or more O, N and S. Preferred 4 to 8 membered heterocycloalkyl groups are 5 or 6 membered heterocycloalkyl groups. Examples of 4 to 8 and 5 or 6 membered heterocycloalkyl groups include but are not limited to optionally substituted azetidinyl, piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiomorpholinyl, thiomorpholinylsulfoxide, thiomorpholinylsulfone, dihydroquinolinyl, dihydrisoquinolinyl, tetrahydroquinolinyl, tetrahydroisoquinolinyl, 1-oxo-thiomorpholin, 1,1-dioxo-thiomorpholin, 1,4-diazepane, 1,4-oxazepane and 8-oxa-3-aza-bicyclo[3.2.1]oct-3-yl, as well as those groups specifically illustrated by the examples herein below.

"$R^6$ together with $R^5$ forms a 5 or 6 membered heterocycloalkyl group" denotes a 5 or 6 membered heterocycloalkyl group as defined above which is fused to the quinoline group via $R^5$ and $R^6$. An example of such group is but is not limited to the following group:

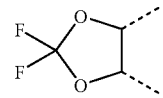

"Pharmaceutically acceptable" such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, which include but are not limited to hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid.

"Therapeutically effective amount" means an amount that is effective to prevent, alleviate or ameliorate symptoms of disease or prolong the survival of the subject being treated.

The present invention provides compounds of formula I

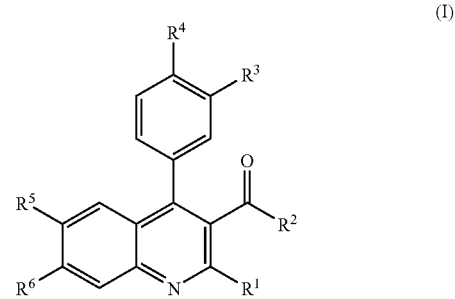

wherein $R^1$ is hydrogen, $C_1$-$C_7$ alkyl, $C_1$-$C_7$ haloalkyl, di($C_1$-$C_7$)alkylamino, $C_3$-$C_8$ cycloalkyl, or a 5 or 6 membered heterocycloalkyl;

$R^2$ is $C_1$-$C_7$ alkyl, aryl, $C_1$-$C_7$ alkoxy($C_1$-$C_7$)alkyl, $C_1$-$C_7$ haloalkyl or $C_3$-$C_8$ cycloalkyl;

R³ and R⁴ are each independently hydrogen, halo, hydroxy, $C_1$-$C_7$ alkoxy, $C_1$-$C_7$ haloalkoxy, di($C_1$-$C_7$)alkylamino, $C_1$-$C_7$ alkylsulfonyl, or a 5 or 6 membered heterocycloalkyl;

R⁵ is hydrogen, halo, $C_1$-$C_7$ alkyl, $C_1$-$C_7$ alkoxy, $C_1$-$C_7$ haloalkoxy, aryloxy, or —NR⁷R⁸ wherein R⁷ and R⁸ are each independently $C_1$-$C_7$ alkyl, or R⁷ and R⁸, together with the nitrogen atom to which they are attached, form or a 4 to 8 membered heterocycloalkyl group which is optionally substituted by one or more subsituent(s) selected from the group consisting of halo, $C_1$-$C_7$ alkyl, $C_1$-$C_7$ alkoxy, hydroxy, phenyl and di($C_1$-$C_7$)alkylamino; and R⁶ is hydrogen or together with R⁵ forms a 5 or 6 membered heterocycloalkyl group which is optionally substituted by one or more halogen;

and pharmaceutically acceptable acid addition salts thereof, excluding the following compounds:

1-(6-Chloro-2-methyl-4-phenyl-quinolin-3-yl)-ethanone;
1-(6-Bromo-4-phenyl-2-piperidin-1-yl-quinolin-3-yl)-ethanone;
1-[4-(4-Chloro-phenyl)-2-methyl-quinolin-3-yl]-ethanone;
1-(6-Bromo-2-methyl-4-phenyl-quinolin-3-yl)-ethanone;
1-(2,6-Dimethyl-4-phenyl-quinolin-3-yl)-ethanone; and
1-(2-Methyl-4-phenyl-6-trifluoromethoxy-quinolin-3-yl)-ethanone.

Preferred groups for R¹ are selected from the group consisting of methyl, ethyl, propyl, i-propyl, butyl, i-butyl, and t-butyl.

Preferred groups for R² are selected from the group consisting of methyl, ethyl, propyl, i-propyl, butyl, i-butyl, t-butyl, cyclopropyl, cyclobutyl, cyclopentyl, cyclohexyl, phenyl, $CHF_2$ and $CF_3$.

Preferred groups for R³ are selected from the group consisting of hydrogen, Cl and F.

Preferred groups for R⁴ are selected from the group consisting of hydrogen, methoxy, methylsulfonyl, Cl and F.

Preferred groups for R⁵ are selected from the group consisting of Br, methyl, ethyl, propyl, i-propyl, butyl, i-butyl, and t-butyl, $CF_3O$, PhO, methoxy, Cl, F and I, and when R⁵ is —NR⁷R⁸, R⁷ and R⁸ together with the nitrogen atom to which they are attached form a group selected from the group consisting of piperidin-1-yl, morpholin-4-yl, pyrrolidin-1-yl, piperazin-1-yl, pyrrolidin-1-yl, azetidine-1-yl, and azepan-1-yl, which may be substituted by one or more F, methyl, ethyl, propyl, i-propyl, butyl, i-butyl, t-butyl, hydroxy, methoxy, phenyl, dimethylamino and 1,4-oxazepane and 8-oxa-3-aza-bicyclo[3.2.1]oct-3-yl.

More preferred groups for R⁵ are selected from the group consisting of Br, I, methyl, ethyl, propyl, i-propyl, butyl, i-butyl, t-butyl, $CF_3O$, PhO, methoxy, Cl and F, and when R⁵ is —NR⁷R⁸, R⁷ and R⁸ together with the nitrogen atom to which they are attached form a group selected from the group consisting of piperidin-1-yl, 3,3-difluoro-piperidin-1-yl, 4-hydroxy-4-methyl-piperidin-1-yl, 4-methoxy-piperidine-1-yl, morpholin-4-yl, pyrrolidin-1-yl, 2-methyl-pyrrolidin-1-yl, 4-methyl-piperazin-1-yl, 3-hydroxy-pyrrolidin-1-yl, 3-hydroxy-azetidine-1-yl, 4-hydroxy-4phenyl-piperidin-1-yl, 3,3-dimethylamine-pyrrolidin-1-yl, azepan-1-yl and 1,4-oxazepane and 8-oxa-3-aza-bicyclo[3.2.1]oct-3-yl.

In one embodiment the invention provides compounds of formula I, wherein

R¹ is $C_1$-$C_7$ alkyl;
R² is $C_1$-$C_7$ alkyl, phenyl, $C_1$-$C_7$ haloalkyl or $C_3$-$C_8$ cycloalkyl;
R³ and R⁴ are each independently hydrogen, halo, $C_1$-$C_7$ alkoxy, or $C_1$-$C_7$ alkylsulfonyl;
R⁵ is halo, $C_1$-$C_7$ haloalkoxy, aryloxy, or is —NR⁷R⁸ wherein R⁷ and R⁸ are each independently $C_1$-$C_7$ alkyl, or R⁷ and R⁸, together with the nitrogen atom to which they are attached, form or a 4 to 8 membered heterocycloalkyl group which is optionally substituted by one or more subsituent(s) selected from the group consisting of halo, $C_1$-$C_7$ alkyl, hydroxy, $C_1$-$C_7$ alkoxy, phenyl and di($C_1$-$C_7$) alkylamino;

R⁶ is hydrogen or together with R⁵ forms a 5 or 6 membered heterocycloalkyl group which is optionally substituted by one or more halogen.

In another embodiment, the invention provides compounds of formula I wherein R² is $C_1$-$C_7$ alkyl, for example the following compounds:

1-(6-Bromo-2-ethyl-4-phenyl-quinolin-3-yl)-propan-1-one;
1-(6-Bromo-2-isobutyl-4-phenyl-quinolin-3-yl)-ethanone;
1-(6-Bromo-2-methyl-4-phenyl-quinolin-3-yl)-3-methyl-butan-1-one;
1-[4-(4-Chloro-phenyl)-2-methyl-6-trifluoromethoxy-quinolin-3-yl]-ethanone;
1-(6-Bromo-2-isopropyl-4-phenyl-quinolin-3-yl)-2-methyl-propan-1-one;
1-[4-(3,4-Dichloro-phenyl)-2-methyl-6-trifluoromethoxy-quinolin-3-yl]-ethanone;
1-[4-(4-Chloro-phenyl)-2-methyl-6-phenoxy-quinolin-3-yl]-ethanone; and
1-[4-(3-Chloro-phenyl)-2-methyl-6-trifluoromethoxy-quinolin-3-yl]-ethanone.

In a further embodiment, the invention provides compounds of formula I wherein, wherein R² is $C_1$-$C_7$ haloalkyl, for example the following compounds:

1-(6-Bromo-2-methyl-4-phenyl-quinolin-3-yl)-2,2,2-trifluoro-ethanone;
1-(6-Bromo-2-methyl-4-phenyl-quinolin-3-yl)-2,2-difluoro-ethanone;
2,2,2-Trifluoro-1-(2-methyl-4-phenyl-6-trifluoromethoxy-quinolin-3-yl)-ethanone;
1-[4-(3-Chloro-phenyl)-2-methyl-6-trifluoromethoxy-quinolin-3-yl]-2,2,2-trifluoro-ethanone;
1-[4-(4-Chloro-phenyl)-2-methyl-6-trifluoromethoxy-quinolin-3-yl]-2,2,2-trifluoro-ethanone;
2,2,2-Trifluoro-1-[4-(4-methoxy-phenyl)-2-methyl-6-trifluoromethoxy-quinolin-3-yl]-ethanone;
2,2,2-Trifluoro-1-[4-(4-fluoro-phenyl)-2-methyl-6-trifluoromethoxy-quinolin-3-yl]-ethanone;
1-(6-tert-Butyl-2-methyl-4-phenyl-quinolin-3-yl)-2,2,2-trifluoro-ethanone;
1-(2,2-Difluoro-6-methyl-8-phenyl-[1,3]dioxolo[4,5-g]quinolin-7-yl)-2,2,2-trifluoro-ethanone;
1-[4-(3,4-Difluoro-phenyl)-2-methyl-6-trifluoromethoxy-quinolin-3-yl]-2,2,2-trifluoro-ethanone;
2,2,2-Trifluoro-1-[4-(4-methanesulfonyl-phenyl)-2-methyl-6-trifluoromethoxy-quinolin-3-yl]-ethanone;
2,2,2-Trifluoro-1-[4-(3-fluoro-4-methoxy-phenyl)-2-methyl-6-trifluoromethoxy-quinolin-3-yl]-ethanone;
2,2,2-Trifluoro-1-(2-methyl-4-phenyl-6-piperidin-1-yl-quinolin-3-yl)-ethanone;
2,2,2-Trifluoro-1-(2-methyl-6-morpholin-4-yl-4-phenyl-quinolin-3-yl)-ethanone;
2,2,2-Trifluoro-1-(2-methyl-4-phenyl-6-pyrrolidin-1-yl-quinolin-3-yl)-ethanone;
2,2,2-Trifluoro-1-[2-methyl-6-(2-methyl-pyrrolidin-1-yl)-4-phenyl-quinolin-3-yl]-ethanone;
2,2,2-Trifluoro-1-[2-methyl-6-(4-methyl-piperazin-1-yl)-4-phenyl-quinolin-3-yl]-ethanone;
2,2,2-Trifluoro-1-[6-(3-hydroxy-pyrrolidin-1-yl)-2-methyl-4-phenyl-quinolin-3-yl]-ethanone;

2,2,2-Trifluoro-1-[6-(3-hydroxy-azetidin-1-yl)-2-methyl-4-phenyl-quinolin-3-yl]-ethanone;
1-[6-Bromo-4-(4-methanesulfonyl-phenyl)-2-methyl-quinolin-3-yl]-2,2,2-trifluoro-ethanone;
1-[6-Bromo-4-(4-fluoro-phenyl)-2-methyl-quinolin-3-yl]-2,2,2-trifluoro-ethanone;
2,2,2-Trifluoro-1-[4-(4-methanesulfonyl-phenyl)-2-methyl-6-piperidin-1-yl-quinolin-3-yl]-ethanone;
2,2,2-Trifluoro-1-[4-(4-fluoro-phenyl)-2-methyl-6-piperidin-1-yl-quinolin-3-yl]-ethanone;
2,2,2-Trifluoro-1-[4-(4-fluoro-phenyl)-2-methyl-6-morpholin-4-yl-quinolin-3-yl]-ethanone;
2,2,2-Trifluoro-1-[4-(4-methanesulfonyl-phenyl)-2-methyl-6-pyrrolidin-1-yl-quinolin-3-yl]-ethanone;
2,2,2-Trifluoro-1-[4-(4-fluoro-phenyl)-2-methyl-6-pyrrolidin-1-yl-quinolin-3-yl]-ethanone;
2,2,2-Trifluoro-1-[4-(4-fluoro-phenyl)-6-(3-hydroxy-pyrrolidin-1-yl)-2-methyl-quinolin-3-yl]-ethanone;
2,2,2-Trifluoro-1-[6-(4-hydroxy-4-phenyl-piperidin-1-yl)-2-methyl-4-phenyl-quinolin-3-yl]-ethanone;
2,2,2-Trifluoro-1-[6-(4-hydroxy-4-phenyl-piperidin-1-yl)-4-(4-methanesulfonyl-phenyl)-2-methyl-quinolin-3-yl]-ethanone;
2,2,2-Trifluoro-1-[4-(4-fluoro-phenyl)-6-(4-hydroxy-4-phenyl-piperidin-1-yl)-2-methyl-quinolin-3-yl]-ethanone;
2,2,2-Trifluoro-1-[4-(4-fluoro-phenyl)-6-(3-hydroxy-azetidin-1-yl)-2-methyl-quinolin-3-yl]-ethanone;
1-[6-Azepan-1-yl-4-(4-fluoro-phenyl)-2-methyl-quinolin-3-yl]-2,2,2-trifluoro-ethanone;
1-(6-Azepan-1-yl-2-methyl-4-phenyl-quinolin-3-yl)-2,2,2-trifluoro-ethanone;
1-[6-(3-Dimethylamino-pyrrolidin-1-yl)-2-methyl-4-phenyl-quinolin-3-yl]-2,2,2-trifluoro-ethanone;
1-[6-(3-Dimethylamino-pyrrolidin-1-yl)-4-(4-methanesulfonyl-phenyl)-2-methyl-quinolin-3-yl]-2,2,2-trifluoro-ethanone;
1-[6-(3-Dimethylamino-pyrrolidin-1-yl)-4-(4-fluoro-phenyl)-2-methyl-quinolin-3-yl]-2,2,2-trifluoro-ethanone;
2,2,2-Trifluoro-1-[6-iodo-4-(4-methanesulfonyl-phenyl)-2-methyl-quinolin-3-yl]-ethanone;
2,2,2-Trifluoro-1-[6-(4-hydroxy-4-methyl-piperidin-1-yl)-4-(4-methanesulfonyl-phenyl)-2-methyl-quinolin-3-yl]-ethanone;
2,2,2-Trifluoro-1-[4-(4-methanesulfonyl-phenyl)-6-(4-methoxy-piperidin-1-yl)-2-methyl-quinolin-3-yl]-ethanone;
1-[6-(3,3-Difluoro-piperidin-1-yl)-4-(4-methanesulfonyl-phenyl)-2-methyl-quinolin-3-yl]-2,2,2-trifluoro-ethanone; and
2,2,2-Trifluoro-1-[4-(4-methanesulfonyl-phenyl)-2-methyl-6-(8-oxa-3-aza-bicyclo[3.2.1]oct-3-yl)-quinolin-3-yl]-ethanone.

In another embodiment, the invention provides compounds of formula I, wherein $R^2$ is $C_3$-$C_8$ cycloalkyl, for example the following compounds:
[6-Bromo-4-(4-methanesulfonyl-phenyl)-2-methyl-quinolin-3-yl]-cyclopropyl-methanone;
Cyclopropyl-[4-(4-methanesulfonyl-phenyl)-2-methyl-6-morpholin-4-yl-quinolin-3-yl]-methanone;
Cyclopropyl-[4-(4-methanesulfonyl-phenyl)-2-methyl-6-piperidin-1-yl-quinolin-3-yl]-methanone;
[(6-Bromo-2-methyl-4-phenyl-quinolin-3-yl)-cyclopropyl-methanone;
[6-Bromo-4-(4-fluoro-phenyl)-2-methyl-quinolin-3-yl]-cyclopropyl-methanone;
Cyclopropyl-(2-methyl-4-phenyl-6-piperidin-1-yl-quinolin-3-yl)-methanone; and
Cyclopropyl-(2-methyl-6-morpholin-4-yl-4-phenyl-quinolin-3-yl)-methanone.

In yet another embodiment, the invention provides compounds of formula I, wherein $R^2$ is phenyl, for example the following compounds:
(6-Bromo-2-methyl-4-phenyl-quinolin-3-yl)-phenyl-methanone; and
[4-(3-Chloro-phenyl)-2-methyl-6-trifluoromethoxy-quinolin-3-yl]-phenyl-methanone.

The afore-mentioned compounds of formula I can be manufactured by the following process of the invention comprising the step of reacting a compound of formula II

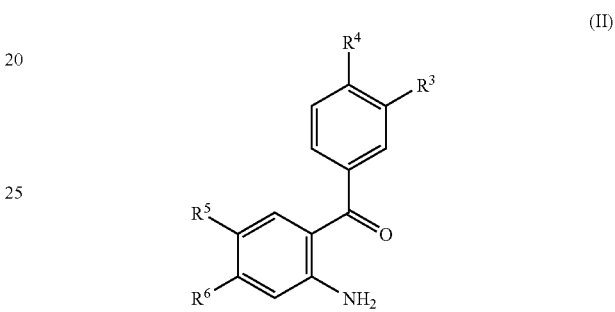

with a compound of formula III

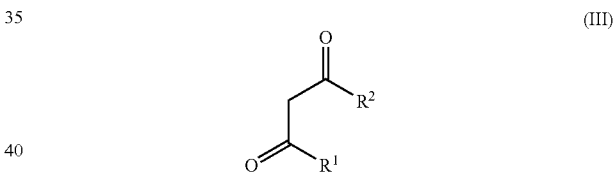

wherein $R^1$ to $R^6$ are as defined in formula I.
to give the compound of formula I;
and if desired, converting the compound of formula I obtained into a pharmaceutically acceptable acid addition salt.

The afore-mentioned compounds of formula I can also be manufactured in accordance with the invention by the following variant process comprising the step of reacting a compound of formula IV

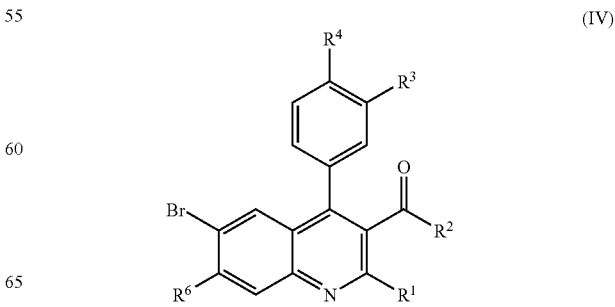

with a compound of formula V

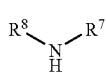
(V)

to give the compound of formula Ia;

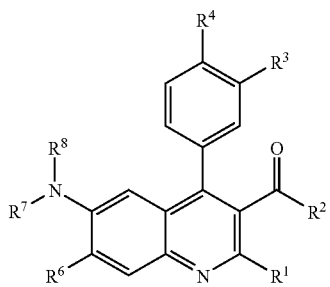
Ia wherein $R^1$ to $R^8$ are as defined in formula I;

and if desired, converting the compound of formula Ia obtained into a pharmaceutically acceptable acid addition salt. It is understood that the compounds of formula Ia correspond to the compounds of formula I wherein $R^5$ is —$NR^7R^8$ and $R^7$ and $R^8$ are as defined for formula I.

The invention also encompasses a compound of formula I or Ia, whenever it is prepared according to the above-mentioned processes.

In the following the preparation of compounds of formula I is described in more detail:

In schemes 1 and 2 are described processes for preparation of compound of formula I or Ia.

The preparation of compounds of formula I are further described in detail in working examples 1-46.

Scheme 1

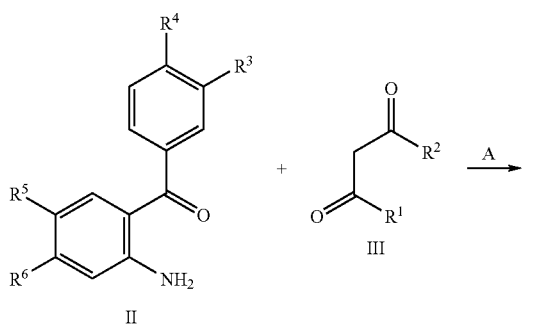

A) cat. (NaAuCl$_4$ 2H$_2$O)

Method A

According to the procedure developed by A. Arcadi, M. Chiarini, S. Di Giuseppe, and F. Marinelli, Synlett 203-206 (2003), the 2-aminobenzophenone (II) is reacted with the 1,3-dione III and sodium tetrachloroaureate(III) dihydrate as catalyst. The residue can be purified by conventional methods.

Scheme 2

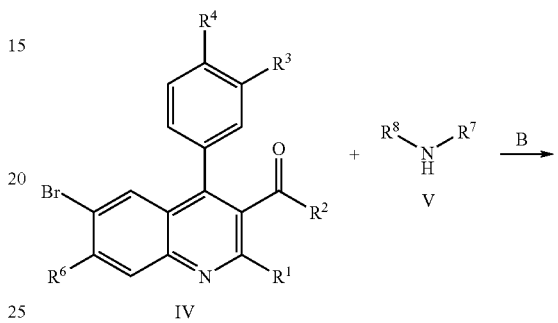

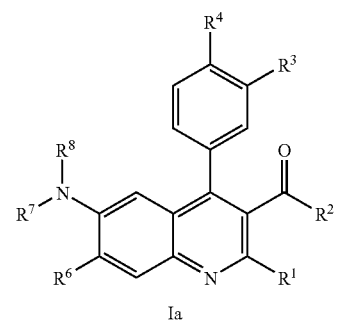
Ia

B) cat. Pd$_2$dba$_3$ CHCl$_3$, rac-BINAP, Cs$_2$CO$_3$

Method B

Following a methodology developed by J. P. Wolfe and S. L. Buchwald (J. Org. Chem. 2000, 65, 1144-1157) tris(dibenzylideneacetone)dipalladium chloroform complex is added to rac-2,2'-bis(diphenylphosphino)-1,1'-binaphthyl, cesium carbonate, the 2-amino-4-bromo-benzoquinone IV, and the amine V. The residue can be purified by conventional methods.

One part of the starting material used in the general procedures of schemes 1 and 2 is commercially available (e.g. some of the benzophenones of formula IV, all 1,3-diketones of formula III, and all the amines of formula V). However the non commercially available part of said starting material can be prepared according to the general procedure of method C for compounds of formula II as outlined hereafter in scheme 3, or according to the general procedure of method A for providing suitable compounds of formula IV as outline hereinabove in scheme 1. Unless otherwise specified, the intermediate compounds described therein are novel compounds:

Scheme 3

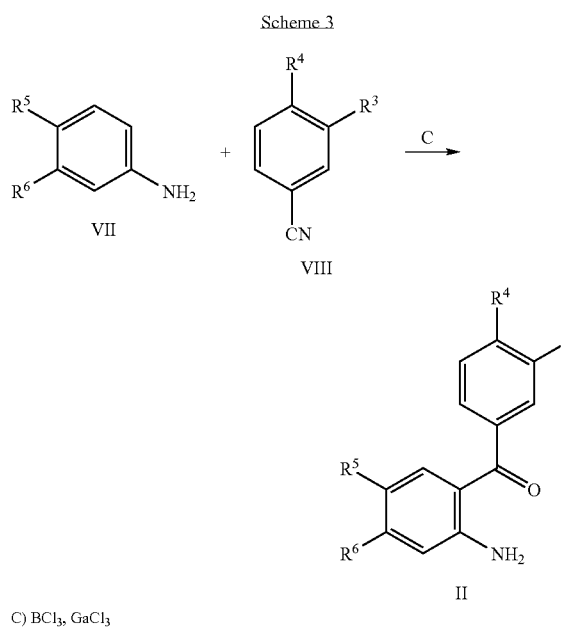

C) BCl₃, GaCl₃

Method C

Following a procedure developed by T. Sugasawa, T. Toyoda, M. Adachi, and K. Sasakura, J. Am. Chem. Soc. 100, 4842-4852 (1978) and improved by A. W. Douglas, N. L. Abramson, I. N. Houpis, S. Karady, A. Molina, L. C. Xavier, N. Yasuda, Tetrahedron Lett. 35, 6807-6810 (1994), either gallium (III) chloride or aluminium (III) chloride are mixed with a chlorinated solvent. Aniline VII, boron trichloride and benzonitrile VIII are then added to the cold mixture. The crude product can be purified by conventional methods.

The preparation of compounds of formula II is further described in detail in working examples A1 to A16.

As mentioned earlier, the compounds of formula I and their pharmaceutically acceptable addition salts possess valuable pharmacological properties. It has been found that the compounds of the present invention have an affinity to the $GABA_B$ receptor.

The compounds were investigated in accordance with the tests given hereinafter.

Intracellular Ca²⁺ Mobilization Assay

The Chinese Hamster Ovary (CHO) cells stably expressing human $GABA_BR1aR2a$ and $G\alpha16$ were seeded at $5\times10^4$ cells/well in the poly-D-lysine treated, 96-well, black/clear-bottomed plates (BD Biosciences, Palo Alto, Calif.). 24 h later, the cells were loaded for 90 min at 37° C. with 4 µM Flou-4 acetoxymethyl ester (Catalog No. F-14202, Molecular Probes, Eugene, Oreg.) in loading buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with loading buffer to remove excess dye and intracellular calcium mobilization, $[Ca^{2+}]_i$ were measured using a Fluorometric Imaging Plate Reader (FLIPR, Molecular Devices, Menlo Park, Calif.) as described previously (Porter et al., Br. J. Pharmacol., 128, 13-20, 1999). The enhancers were applied 15 min before the application of the GABA. For GABA shift assay, concentration-response curves of GABA (0.0003-30 µM) were determined in the absence and presence of 10 M enhancer. The GABA-shift is defined as Log $[EC_{50}$ (GABA+10 µM enhancer)/$EC_{50}$ (GABA alone)]. The % maximum enhancing effect (% $E_{max}$) and potency ($EC_{50}$ value) of each enhancer was determined from concentration-response curve of the enhancer (0.001-30 µM) in the presence of 10 nM GABA ($EC_{10}$). Responses were measured as peak increase in fluorescence minus basal, normalized to the maximal stimulatory effect induced by 10 µM GABA alone (considered 100%) and 10 nM GABA alone (considered 0%). The data were fitted with the equation $Y=100+(Max-100)/(1+(EC_{50}/[drug])^n)$ where Max is the maximum effect, $EC_{50}$ the concentration eliciting a half-maximum effect and n the Hill slope.

| | Intracellular Ca²⁺ mobilization Assay in CHO-GABA$_B$R1aR2a-Gα16 cell | | |
|---|---|---|---|
| Example | $E_{max}$ (%) at 10 nM GABA alone = 0% 10 µM GABA alone = 100% | $EC_{50}$ (µM) at 10 nM GABA | GABA shift Log [$EC_{50}$(GABA + 10 µM cp)/$EC_{50}$(GABA alone)] |
| 3 | 124 | 0.80 | −1.20 |
| 11 | 65 | 0.80 | −1.00 |
| 15 | 67 | 1.60 | −1.15 |
| 19 | 63 | 0.90 | −0.70 |
| 33 | 62 | 0.33 | −0.90 |
| 56 | 58 | 2.20 | −0.90 |

The present invention also provides pharmaceutical compositions containing compounds of the invention, for example compound of formula I or a pharmaceutically acceptable acid addition salt thereof, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatin capsules.

Suitable excipients for soft gelatin capsules are e.g. vegetable oils, waxes, fats, semi-solid and liquid polyols.

Suitable excipients for the manufacture of solutions and syrups include but are not limited to water, polyols, saccharose, invert sugar, glucose.

Suitable excipients for injection solutions include but are not limited to water, alcohols, polyols, glycerol, vegetable oils.

Suitable excipients for suppositories include but are not limited to natural or hardened oils, waxes, fats, semi-liquid or liquid polyols.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention provides a method of treating a disorder selected from the group consisting of anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders and gastro-intestinal disorders which comprises administering to an individual a therapeutically effective amount of a compound of formula I. In particular, a method of treating a disorder selected from the group consisting of anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders and gastro-intestinal disorders which comprises administering to an individual a therapeutically effective amount of a compound selected from the group consisting of 1-(6-Chloro-2-methyl-4-phenyl-quinolin-3-yl)-ethanone; 1-(6-Bromo-4-phenyl-2-piperidin-1-yl-quinolin-3-yl)-ethanone; 1-[4-(4-Chloro-phenyl)-2-methyl-quinolin-3-yl]-ethanone; 1-(6-Bromo-2-methyl-4-phenyl-quinolin-3-yl)-ethanone; 1-(2,6-Dimethyl-4-phenyl-quinolin-3-yl)-ethanone; and 1-(2-Methyl-4-phenyl-6-trifluoromethoxy-quinolin-3-yl)-ethanone or a pharmaceutically acceptable acid addition salt thereof.

The compounds and compositions of the present invention can be administered in a conventional manner, for example, orally, rectally, or parenterally. The compounds of the invention can be administered orally, for example, in the form of tablets, coated tablets, dragées, hard and soft gelatine capsules, solutions, emulsions, or suspensions. The compounds of the invention can be administered rectally, for example, in the form of suppositories or parenterally, for example, in the form of injectable solutions.

The dosage at which the compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLES

Synthesis of Intermediates of Formula II

Example A1

(2-Amino-5-tert-butyl-phenyl)-phenyl-methanone

The title compound was prepared following the general procedure of method C. In a glass flask fitted with magnetic stir bar, rubber septum, thermometer, Hickmann-condenser, nitrogen-purged bubbler connected to a washing bottle containing 30% NaOH, the content of a fresh ampoule of gallium (III) chloride (5 g, 29 mmol) was added at once and then dissolved by the addition of 1,2-dichloroethane (80 mL). This solution was cooled in ice, then 4-tert-butylaniline (36 mmol) was added slowly while keeping the temperature below 5° C. Then the solution was cooled to −10° C. and a fresh 1 M solution of boron trichloride in dichloromethane (27 mL) was added via a syringe fitted with a teflon stop-cock while keeping the temperature below −5° C. Finally benzonitrile was added (24 mmol) and the mixture was allowed to warm to 20° C. The Hickmann-condenser was replaced by a normal reflux condenser and the reaction mixture was heated in an oil-bath (90° C.) over 1-2 h in order to distil off all the dichloromethane (a total of ca. 50 mL of distillate was collected) until the reflux temperature of 80° C. was achieved. Refluxing was continued for 14 h. The reaction mixture was cooled in ice and hydrolyzed slowly with water (40 mL) and then heated at 60-80° C. for 20-30 min. in order to hydrolyze the imine. The reaction mixture was cooled again and then extracted with dichloromethane and water. The crude product was purified by chromatography on silica gel in heptane/ethylaceteate (4:1) and the purified product (yield 40%) analyzed by MS: m/z=254 (M+H).

Example A2

(2-Amino-5-bromo-phenyl)-(4-fluoro-phenyl)-methanone

The title compound was prepared by reacting 4-bromoaniline and 4-methylsulfonyl benzonitrile following to the procedure of example A1. Yield 37%; MS: m/z=294 (M).

Example A3

(2-Amino-5-trifluoromethoxy-phenyl)-(4-chloro-phenyl)-methanone

The title compound was prepared by reacting 4-(trifluoromethoxy)aniline and 4-chloro benzonitrile following to the procedure of example A1, except that Aluminium (III) chloride was used, that the reaction time was 4 h and heptane/ethylaceteate (2:1) was used for the chromatography. Yield 18%; MS: m/z=315 (M).

Example A4

(2-Amino-5-trifluoromethoxy-phenyl)-(3,4-dichloro-phenyl)-methanone

The title compound was prepared by reacting 4-(trifluoromethoxy)aniline and 3,4-dichloro benzonitrile following to the procedure of example A3, except that the reaction time was 16 h. Yield 15%; MS: m/z=408 (M+OAc).

Example A5

(2-Amino-5-phenoxy-phenyl)-(4-chloro-phenyl)-methanone

The title compound was prepared by reacting 4-phenoxyaniline and 4-chloro benzonitrile following to the procedure of example A3, except that the reaction time was 14 h and a gradient of heptane/ethylaceteate was used for the chromatography. Yield 38%; MS: m/z=324 (M+H).

Example A6

(2-Amino-5-trifluoromethoxy-phenyl)-phenyl-methanone

The title compound is known from FR 7666 and was prepared by reacting 4-(trifluoromethoxy)aniline and benzonitrile following to the procedure of example A1, except that the reaction time was 16 h and heptane/ethylaceteate (5:1) was used for the chromatography. Yield 40%; MS: m/z=282 (M+H).

Example A7

(2-Amino-5-trifluoromethoxy-phenyl)-(3-chloro-phenyl)-methanone

The title compound was prepared by reacting 4-(trifluoromethoxy)aniline and 3-chloro-benzonitrile following to the procedure of example A1. Yield 19%; MS: m/z=315 (M).

Example A8

(2-Amino-5-trifluoromethoxy-phenyl)-(4-methoxy-phenyl)-methanone

The title compound was prepared by reacting 4-phenoxyaniline and 4-methoxy benzonitrile following to the procedure of example A1, except that the reaction time was 19 h and a gradient of heptane/ethylaceteate was used for the chromatography. Yield 19%; MS: m/z=312 (M+H).

Example A9

(2-Amino-5-trifluoromethoxy-phenyl)-(4-fluoro-phenyl)-methanone

The title compound was prepared by reacting 4-(trifluoromethoxy)aniline and 4-fluorobenzonitrile following to the procedure of example A1. Yield 26%; MS: m/z=299 (M).

Example A10

(6-Amino-2,2-difluoro-benzo[1,3]dioxol-5-yl)-phenyl-methanone

The title compound was prepared by reacting 2,2-difluoro-5-aminobenzodioxole and benzonitrile following to the procedure of example A1. Yield 1.5%; MS: m/z=366 (M+OAc).

Example A11

(2-Amino-5-trifluoromethoxy-phenyl)-(3-trifluoromethoxy-phenyl)-methanone

The title compound was prepared by reacting 4-(trifluoromethoxy)aniline and 3-(trifluoromethoxy)benzonitrile following to the procedure of example A1. Yield 29%; MS: m/z=365 (M).

Example A12

(2-Amino-5-trifluoromethoxy-phenyl)-(3,4-difluoro-phenyl)-methanone

The title compound was prepared by reacting 4-(trifluoromethoxy)aniline and 3,4-difluorobenzonitrile following to the procedure of example A1. Yield 36%; MS: m/z=317 (M).

Example A13

(2-Amino-5-trifluoromethoxy-phenyl)-(4-methanesulfonyl-phenyl)-methanone

The title compound was prepared by reacting 4-(trifluoromethoxy)aniline and 4-methylsulfonylbenzonitrile following to the procedure of example A1. Yield 71%; MS: m/z=359 (M).

Example A14

(2-Amino-5-trifluoromethoxy-phenyl)-(3-fluoro-4-methoxy-phenyl)-methanone

The title compound was prepared by reacting 4-(trifluoromethoxy)aniline and 3-methoxybenzonitrile following to the procedure of example A1. Yield 19%; MS: m/z=329 (M).

Example A15

(2-Amino-5-bromo-phenyl)-(4-methanesulfonyl-phenyl)-methanone

The title compound was prepared by reacting 4-bromoaniline and 4-methylsulfonylbenzonitrile following to the procedure of example A1. Yield 51%; MS: m/z=355 (M+H).

Example A16

(2-Amino-5-bromo-phenyl)-phenyl-methanone

The title compound is known from US 20040127536 A1 and was prepared according to a method developed by D. Roche, K. Prasad, O. Repic, T. J. Blacklock, *Tetrahedron Lett.* 41, 2083-2085 (2000). 2-Aminobenzophenone (30 g, 152 mmol) was suspended in acetic acid (300 mL). Potassium bromide (19.9 g, 167 mmol), sodium perborate tetrahydrate (28 g, 183 mmol) and ammonium molybdate tetrahydrate (1.5 g) were added and stirring continued for 3 hours at 0° C. The dense yellow precipitate which formed was diluted with ice water (300 mL) and then filtered off and washed with ice water and dried. One obtained 40.3 g (96%) of a yellow solid. MS: m/z=276 (M).

Example A17

(2-Amino-5-iodo-phenyl)-(4-methanesulfonyl-phenyl)-methanone

The title compound was prepared by reacting 4-iodoaniline and 4-methylsulfonylbenzonitrile following to the procedure of example A1. Yield 31%; MS: m/z=402 (M+H).

Synthesis of Compounds of Formula I According to the Invention

Example 1

1-(6-Bromo-2-ethyl-4-phenyl-quinolin-3-yl)-propan-1-one

The title compound was prepared according to the general procedure of method A. The (2-Amino-5-bromo-phenyl)-phenyl-methanone [example A16] (on 0.1-1 g scale) and 3,5-heptanedione (1.5 equiv) and sodium tetrachloroaureate(III) dihydrate (0.025 equiv) were heated in parallel in a Radley carousel under nitrogen in ethanol (10% w/w-solution of (2-Amino-5-bromo-phenyl)-phenyl-methanone) and reacted for 24 h. The reaction mixture was evaporated to dryness and the residue purified by chromatography on silica gel in heptane/ethyl acetate (20:1). Yield: 37%. MS: m/z=368 (M).

Example 2

(6-Bromo-2-methyl-4-phenyl-quinolin-3-yl)-phenyl-methanone

The title compound was prepared from (2-Amino-5-bromo-phenyl)-phenyl-methanone [example A16] and 1-phenyl-1,3-butanedione, except that the residue was purified by spontaneous crystallization from the reaction mixture. Yield: 61%; MS: m/z=402 (M+H).

Example 3

1-(6-Bromo-2-methyl-4-phenyl-quinolin-3-yl)-2,2,2-trifluoro-ethanone

The title compound was prepared from (2-Amino-5-bromo-phenyl)-phenyl-methanone [example A16] and 1,1,1-trifluoro-2,4-pentanedione according to the procedure of example 1, except that heptane/ethyl acetate (10:1) was used. Yield: 50%; MS: m/z=392/394 (M).

Example 4

1-(6-Bromo-2-isobutyl-4-phenyl-quinolin-3-yl)-ethanone

The title compound was prepared from (2-Amino-5-bromo-phenyl)-phenyl-methanone [example A16] and 6-methyl-2,4-heptanedione according to the procedure of example 1. Yield: 9%. MS: m/z=381 (M).

Example 5

1-(6-Bromo-2-methyl-4-phenyl-quinolin-3-yl)-3-methyl-butan-1-one

The title compound was prepared from (2-Amino-5-bromo-phenyl)-phenyl-methanone [example A16] and 6-methyl-2,4-heptanedione according to the procedure of example 1. Yield: 55%. MS: m/z=381 (M).

Example 6

1-(6-Bromo-2-methyl-4-phenyl-quinolin-3-yl)-2,2-difluoro-ethanone

The title compound was prepared from (2-Amino-5-bromo-phenyl)-phenyl-methanone [example A16] and 1,1-difluoroacetylacetone according to the procedure of example 1, except that the residue was purified by chromatography on aminated silica gel with heptane/ethyl acetate (5:1). Yield: 36%. MS: m/z=377 (M).

Example 7

1-[4-(4-Chloro-phenyl)-2-methyl-6-trifluoromethoxy-quinolin-3-yl]-ethanone

The title compound was prepared from (2-Amino-5-trifluoromethoxy-phenyl)-(4-chloro-phenyl)-methanone [example A3] and acetylacetone according to the method of example 1, except that heptane/ethyl acetate (1:2) was used. Yield: 61%. MS: m/z=379 (M).

Example 8

1-(6-Bromo-2-isopropyl-4-phenyl-quinolin-3-yl)-2-methyl-propan-1-one

The title compound was prepared from (2-Amino-5-bromo-phenyl)-phenyl-methanone [example A16] and 2,6-dimethyl-3,5-heptanedione according to the method of example 1, except that the reaction time was of 96 h and the residue was purified by chromatography on aminated silica gel with heptane/ethyl acetate (85:15). Yield: 46%. MS: m/z=395/397 (M).

Example 9

1-[4-(3,4-Dichloro-phenyl)-2-methyl-6-trifluoromethoxy-quinolin-3-yl]-ethanone

The title compound was prepared from (2-Amino-5-trifluoromethoxy-phenyl)-(3,4-dichloro-phenyl)-methanone [example A4] and acetylacetone according to the method of example 1, except that heptane/ethyl acetate (1:2). Yield: 59%. MS: m/z=414 (M).

Example 10

1-[4-(4-Chloro-phenyl)-2-methyl-6-phenoxy-quinolin-3-yl]-ethanone

The title compound was prepared from (2-Amino-5-phenoxy-phenyl)-(4-chloro-phenyl)-methanone [example A5] and acetylacetone according to the method of example 1, except that the solvent was isopropanol, the reaction time was of 16.5 h and the residue was purified by spontaneous crystallization from the reaction mixture. Yield: 42%; MS: m/z=387 (M).

Example 11

2,2,2-Trifluoro-1-(2-methyl-4-phenyl-6-trifluoromethoxy-quinolin-3-yl)-ethanone

The title compound was prepared from (2-Amino-5-trifluoromethoxy-phenyl)-phenyl-methanone [example A6] and 1,1,1-trifluoro-2,4-pentanedione according to the procedure of example 1, except that the reaction time was of 44 h and heptane/ethyl acetate (10:1) was used. Yield: 63%; MS: m/z=399 (M).

Example 12

1-[4-(3-Chloro-phenyl)-2-methyl-6-trifluoromethoxy-quinolin-3-yl]-2,2,2-trifluoro-ethanone The title compound was prepared from (2-Amino-5-trifluoromethoxy-phenyl)-(3-chloro-phenyl)-methanone [example A7] and 1,1,1-trifluoro-2,4-pentanedione according to the procedure of example 1, except that the solvent was isopropanol, the reaction time was of 60 h and heptane/ethyl acetate (1:2) was used. Yield: 58%; MS: m/z=433 (M).

Example 13

[4-(3-Chloro-phenyl)-2-methyl-6-trifluoromethoxy-quinolin-3-yl]-phenyl-methanone The title compound was prepared from (2-Amino-5-trifluoromethoxy-phenyl)-(3-chloro-phenyl)-methanone [example A7] and benzoylacetone according to the procedure of example 1, except that the solvent was isopropanol, and heptane/ethyl acetate (1:2) was used. Yield: 57%; MS: m/z=441 (M).

Example 14

1-[4-(4-Chloro-phenyl)-2-methyl-6-trifluoromethoxy-quinolin-3-yl]-2,2,2-trifluoro-ethanone The title compound was prepared from (2-Amino-5-trifluoromethoxy-phenyl)-(4-chloro-phenyl)-methanone [example A3] and 1,1,1-trifluoro-2,4-pentanedione according to the procedure of example 1, except that the solvent was isopropanol, the reaction time was of 16 h and heptane/ethyl acetate (1:2) was used. Yield: 34%; MS: m/z=433 (M).

Example 15

1-[4-(3-Chloro-phenyl)-2-methyl-6-trifluoromethoxy-quinolin-3-yl]-ethanone

The title compound was prepared from (2-Amino-5-trifluoromethoxy-phenyl)-(3-chloro-phenyl)-methanone [example A7] and acetylacetone according to the procedure of example 1, except that the solvent was isopropanol, and heptane/ethyl acetate (1:2) was used. Yield: 55%; MS: m/z=380 (M+H).

Example 16

2,2,2-Trifluoro-1-[4-(4-methoxy-phenyl)-2-methyl-6-trifluoromethoxy-quinolin-3-yl]-ethanone The title compound was prepared from (2-Amino-5-trifluoromethoxy-phenyl)-(4-methoxy-phenyl)-methanone [example A8] and 1,1,1-trifluoro-2,4-pentanedione according to the procedure of example 1, except that the solvent was isopropanol, the reaction time was of 17 h and a grandient of heptane/ethyl acetate was used. Yield: 58%; MS: m/z=429 (M).

Example 17

2,2,2-Trifluoro-1-[4-(4-fluoro-phenyl)-2-methyl-6-trifluoromethoxy-quinolin-3-yl]-ethanone The title compound was prepared from (2-Amino-5-trifluoromethoxy-phenyl)-(4-fluoro-phenyl)-methanone [example A9] and 1,1,1-trifluoro-2,4-pentanedione according to the procedure of example 1, except that the solvent was isopropanol, the reaction time was of 16 h and heptane/ethyl acetate (1:2) was used. Yield: 96%; MS: m/z=417 (M).

Example 18

1-(6-tert-Butyl-2-methyl-4-phenyl-quinolin-3-yl)-2,2,2-trifluoro-ethanone

The title compound was prepared from (2-Amino-5-tert-butyl-phenyl)-phenyl-methanone [example A1] and 1,1,1-trifluoro-2,4-pentanedione according to the procedure of example 1, except that the solvent was isopropanol, the reaction time was of 16 h and heptane/ethyl acetate (1:2) was used. Yield: 37%; MS: m/z=372 (M+H).

Example 19

1-(2,2-Difluoro-6-methyl-8-phenyl-[1,3]dioxolo[4,5-g]quinolin-7-yl)-2,2,2-trifluoro-ethanone The title compound was prepared from (6-Amino-2,2-difluoro-benzo[1,3]dioxol-5-yl)-phenyl-methanone [example A10] and 1,1,1-trifluoro-2,4-pentanedione according to the procedure of example 1, except that the solvent was isopropanol, the reaction time was of 16 h and heptane/ethyl acetate (1:2) was used. Yield: 30%; MS: m/z=396 (M+H).

Example 20

1-[4-(3,4-Difluoro-phenyl)-2-methyl-6-trifluoromethoxy-quinolin-3-yl]-2,2,2-trifluoro-ethanone The title compound was prepared from (2-Amino-5-trifluoromethoxy-phenyl)-(3,4-difluoro-phenyl)-methanone [example A12] and 1,1,1-trifluoro-2,4-pentanedione according to the procedure of example 1, except that the solvent was isopropanol, the reaction time was of 16 h and heptane/ethyl acetate (1:2) was used. Yield: 36%; MS: m/z=435 (M).

Example 21

2,2,2-Trifluoro-1-[4-(4-methanesulfonyl-phenyl)-2-methyl-6-trifluoromethoxy-quinolin-3-yl]-ethanone The title compound was prepared from (2-Amino-5-trifluoromethoxy-phenyl)-(4-methanesulfonyl-phenyl)-methanone [example A 13] and 1,1,1-trifluoro-2,4-pentanedione according to the procedure of example 1, except that the solvent was isopropanol, the reaction time was of 16 h and heptane/ethyl acetate (1:2) was used. Yield: 45%; MS: m/z=477 (M).

Example 22

2,2,2-Trifluoro-1-[4-(3-fluoro-4-methoxy-phenyl)-2-methyl-6-trifluoromethoxy-quinolin-3-yl]-ethanone The title compound was prepared from (2-Amino-5-trifluoromethoxy-phenyl)-(4-methanesulfonyl-phenyl)-methanone [example A 14] and 1,1,1-trifluoro-2,4-pentanedione according to the procedure of example 1, except that the solvent was isopropanol, the reaction time was of 16 h and heptane/ethyl acetate (1:2) was used. Yield: 62%; MS: m/z=477 (M).

Example 23

1-[6-Bromo-4-(4-methanesulfonyl-phenyl)-2-methyl-quinolin-3-yl]-2,2,2-trifluoro-ethanone The title compound was prepared from (2-Amino-5-bromo-phenyl)-(4-methanesulfonyl-phenyl)-methanone [example A 15] and 1,1,1-trifluoro-2,4-pentanedione according to the procedure of example 1, except that the solvent was isopropanol, the reaction time was of 16 h and heptane/ethyl acetate (1:2) was used. Yield: 55%; MS: m/z=473 (M+H).

Example 24

1-[6-Bromo-4-(4-fluoro-phenyl)-2-methyl-quinolin-3-yl]-2,2,2-trifluoro-ethanone

The title compound was prepared from (2-Amino-5-bromo-phenyl)-(4-fluoro-phenyl)-methanone [example A2] and 1,1,1-trifluoro-2,4-pentanedione according to the procedure of example 1, except that the solvent was isopropanol, the reaction time was of 16 h and heptane/ethyl acetate (1:2) was used. Yield: 80%; MS: m/z=411/413 (M).

Example 25

2,2,2-Trifluoro-1-(2-methyl-4-phenyl-6-piperidin-1-yl-quinolin-3-yl)-ethanone

The title compound was prepared according to the general procedure of method B. Following a methodology developed by J. P. Wolfe and S. L. Buchwald (*J. Org. Chem.* 2000, 65, 1144-1157) a screw-topped pressure-resistant glass vial (50 mL) equipped with a magnetic stirring bar was flushed with a stream of argon and charged with tris(dibenzylideneacetone) dipalladium chloroform complex (0.01 mmol), rac-2,2'-bis(diphenylphosphino)-1,1'-binaphthyl (0.02 mmol), dioxane (7.5 mL) and tert.-butanol (7.5 mL) and then stirred for 1 min before adding cesium carbonate (1.4 mmol), 1-(6-Bromo-2-methyl-4-phenyl-quinolin-3-yl)-2,2,2-trifluoro-ethanone [example 3] (1 mmol), and piperidine (1.2 mmol). The glass vial was covered with a pressure-resistant seal, firmly locked by a screw-cap and heated with stirring in an oil bath at 120° C. during 2 h. The glass vial was cooled in ice before opening, the reaction mixture was diluted with heptane (5 mL) and filtered through a plug of Dicalite filter-aid and rinsed with heptane. The filtrate was evaporated and the residue purified by chromatography on silica gel in heptane/ethyl acetate (4:1). Yield: 74%; MS: m/z=399 (M+H).

Example 26

2,2,2-Trifluoro-1-(2-methyl-6-morpholin-4-yl-4-phenyl-quinolin-3-yl)-ethanone

The title compound was prepared from 1-(6-Bromo-2-methyl-4-phenyl-quinolin-3-yl)-2,2,2-trifluoro-ethanone [example 3] and morpholine according to the procedure of example 25. Yield: 49%; MS: m/z=401 (M+H).

Example 27

2,2,2-Trifluoro-1-(2-methyl-4-phenyl-6-pyrrolidin-1-yl-quinolin-3-yl)-ethanone

The title compound was prepared from 1-(6-Bromo-2-methyl-4-phenyl-quinolin-3-yl)-2,2,2-trifluoro-ethanone [example 3] and pyrrolidine according to the procedure of example 25. Yield: 56%; MS: m/z=385 (M+H).

Example 28

2,2,2-Trifluoro-1-[2-methyl-6-(2-methyl-pyrrolidin-1-yl)-4-phenyl-quinolin-3-yl]-ethanone The title compound was prepared from 1-(6-Bromo-2-methyl-4-phenyl-quinolin-3-yl)-2,2,2-trifluoro-ethanone [example 3] and 2-methylpyrrolidine according to the procedure of example 25, except that the reaction time was of 16 h. Yield: 21%; MS: m/z=399. (M+H).

Example 29

2,2,2-Trifluoro-1-[2-methyl-6-(4-methyl-piperazin-1-yl)-4-phenyl-quinolin-3-yl]-ethanone The title compound was prepared from 1-(6-Bromo-2-methyl-4-phenyl-quinolin-3-yl)-2,2,2-trifluoro-ethanone [example 3] and N-methylpiperazine according to the procedure of example 25, except that the reaction time was of 16 h. Yield: 73%; MS: m/z=414 (M+H).

Example 30

2,2,2-Trifluoro-1-[6-(3-hydroxy-pyrrolidin-1-yl)-2-methyl-4-phenyl-quinolin-3-yl]-ethanone

The title compound was prepared from 1-(6-Bromo-2-methyl-4-phenyl-quinolin-3-yl)-2,2,2-trifluoro-ethanone [example 3] and 3-pyrrolidinol according to the procedure of example 25, except that the reaction time was of 16 h. Yield: 92%; MS: m/z=401 (M+H).

Example 31

2,2,2-Trifluoro-1-[6-(3-hydroxy-azetidin-1-yl)-2-methyl-4-phenyl-quinolin-3-yl]-ethanone

The title compound was prepared from 1-(6-Bromo-2-methyl-4-phenyl-quinolin-3-yl)-2,2,2-trifluoro-ethanone [example 3] and azetidin-3-ol according to the procedure of example 25, except that the reaction time was of 16 h. Yield: 22%; MS: m/z=387 (M+H).

Example 32

2,2,2-Trifluoro-1-[4-(4-methanesulfonyl-phenyl)-2-methyl-6-piperidin-1-yl-quinolin-3-yl]-ethanone

The title compound was prepared from 1-[6-Bromo-4-(4-methanesulfonyl-phenyl)-2-methyl-quinolin-3-yl]-2,2,2-trifluoro-ethanone [example 23] and piperidine according to the procedure of example 25, except that the reaction time was of 16 h. Yield: 36%; MS: m/z=277 (M+H).

Example 33

2,2,2-Trifluoro-1-[4-(4-fluoro-phenyl)-2-methyl-6-piperidin-1-yl-quinolin-3-yl]-ethanone

The title compound was prepared from 1-[6-Bromo-4-(4-fluoro-phenyl)-2-methyl-quinolin-3-yl]-2,2,2-trifluoro-ethanone [example 24] and piperidine according to the procedure of example 25, except that the reaction time was of 16 h. Yield: 84%; MS: m/z=417 (M+H).

Example 34

2,2,2-Trifluoro-1-[4-(4-fluoro-phenyl)-2-methyl-6-morpholin-4-yl-quinolin-3-yl]-ethanone

The title compound was prepared from 1-[6-Bromo-4-(4-fluoro-phenyl)-2-methyl-quinolin-3-yl]-2,2,2-trifluoro-ethanone [example 24] and morpholine according to the procedure of example 25, except that the reaction time was of 16 h. Yield: 75%; MS: m/z=419 (M+H).

Example 35

2,2,2-Trifluoro-1-[4-(4-methanesulfonyl-phenyl)-2-methyl-6-pyrrolidin-1-yl-quinolin-3-yl]-ethanone

The title compound was prepared from 1-[6-Bromo-4-(4-methanesulfonyl-phenyl)-2-methyl-quinolin-3-yl]-2,2,2-trifluoro-ethanone [example 23] and pyrrolidine according to the procedure of example 25, except that the reaction time was of 16 h. Yield: 51%; MS: m/z=463 (M+H).

Example 36

2,2,2-Trifluoro-1-[4-(4-fluoro-phenyl)-2-methyl-6-pyrrolidin-1-yl-quinolin-3-yl]-ethanone

The title compound was prepared from 1-[6-Bromo-4-(4-fluoro-phenyl)-2-methyl-quinolin-3-yl]-2,2,2-trifluoro-ethanone [example 24] and pyrrolidine according to the procedure of example 25, except that the reaction time was of 16 h. Yield: 64%; MS: m/z=403 (M+H).

Example 37

2,2,2-Trifluoro-1-[4-(4-fluoro-phenyl)-6-(3-hydroxy-pyrrolidin-1-yl)-2-methyl-quinolin-3-yl]-ethanone

The title compound was prepared from 1-[6-Bromo-4-(4-fluoro-phenyl)-2-methyl-quinolin-3-yl]-2,2,2-trifluoro-ethanone [example 24] and 3-pyrrolidinol according to the procedure of example 25, except that the reaction time was of 16 h. Yield: 39%; MS: m/z=419 (M+H).

Example 38

2,2,2-Trifluoro-1-[6-(4-hydroxy-4-phenyl-piperidin-1-yl)-2-methyl-4-phenyl-quinolin-3-yl]-ethanone

The title compound was prepared from 1-[6-Bromo-4-(4-phenyl)-2-methyl-quinolin-3-yl]-2,2,2-trifluoro-ethanone [example 24] and 4-hydroxy-4-phenylpiperidine according to the procedure of example 25, except that the reaction time was of 16 h. Yield: 29%; MS: m/z=491 (M+H).

Example 39

2,2,2-Trifluoro-1-[6-(4-hydroxy-4-phenyl-piperidin-1-yl)-4-(4-methanesulfonyl-phenyl)-2-methyl-quinolin-3-yl]-ethanone

The title compound was prepared from 1-[6-Bromo-4-(4-methanesulfonyl-phenyl)-2-methyl-quinolin-3-yl]-2,2,2-trifluoro-ethanone [example 24] and 4-hydroxy-4-phenylpiperidine according to the procedure of example 25, except that the reaction time was of 16 h. Yield: 17%; MS: m/z=569 (M+H).

Example 40

2,2,2-Trifluoro-1-[4-(4-fluoro-phenyl)-6-(4-hydroxy-4-phenyl-piperidin-1-yl)-2-methyl-quinolin-3-yl]-ethanone

The title compound was prepared from 1-[6-Bromo-4-(4-fluoro-phenyl)-2-methyl-quinolin-3-yl]-2,2,2-trifluoro-ethanone [example 24] and 4-hydroxy-4-phenylpiperidine according to the procedure of example 25, except that the reaction time was of 16 h. Yield: 32%; MS: m/z=509 (M+H).

Example 41

2,2,2-Trifluoro-1-[4-(4-fluoro-phenyl)-6-(3-hydroxy-azetidin-1-yl)-2-methyl-quinolin-3-yl]-ethanone

The title compound was prepared from 1-[6-Bromo-4-(4-fluoro-phenyl)-2-methyl-quinolin-3-yl]-2,2,2-trifluoro-ethanone [example 24] and azetidin-3-ol according to the procedure of example 25, except that the reaction time was of 12 h. Yield: 12%; MS: m/z=405 (M+H).

Example 42

1-[6-Azepan-1-yl-4-(4-fluoro-phenyl)-2-methyl-quinolin-3-yl]-2,2,2-trifluoro-ethanone The title compound was prepared from 1-[6-Bromo-4-(4-fluoro-phenyl)-2-methyl-quinolin-3-yl]-2,2,2-trifluoro-ethanone [example 24] and azepane according to the procedure of example 25, except that the reaction time was of 16 h. Yield: 32%; MS: m/z=431 (M+H).

Example 43

1-(6-Azepan-1-yl-2-methyl-4-phenyl-quinolin-3-yl)-2,2,2-trifluoro-ethanone

The title compound was prepared from 1-(6-Bromo-2-methyl-4-phenyl-quinolin-3-yl)-2,2,2-trifluoro-ethanone [example 3] and azepane according to the procedure of example 25, except that the reaction time was of 16 h. Yield: 14%; MS: m/z=413 (M+H).

Example 44

1-[6-(3-Dimethylamino-pyrrolidin-1-yl)-2-methyl-4-phenyl-quinolin-3-yl]-2,2,2-trifluoro-ethanone The title compound was prepared from 1-(6-Bromo-2-methyl-4-phenyl-quinolin-3-yl)-2,2,2-trifluoro-ethanone [example 3] and 3-(dimethylamino)pyrrolidine according to the procedure of example 25, except that the reaction time was of 16 h and that ethyl acetate/methanol (9:1) was used. Yield: 37%; MS: m/z=428 (M+H).

Example 45

1-[6-(3-Dimethylamino-pyrrolidin-1-yl)-4-(4-methanesulfonyl-phenyl)-2-methyl-quinolin-3-yl]-2,2,2-trifluoro-ethanone The title compound was prepared from 1-[6-Bromo-4-(4-methanesulfonyl-phenyl)-2-methyl-quinolin-3-yl]-2,2,2-trifluoro-ethanone [example 23] and 3-(dimethylamino)pyrrolidine according to the procedure of example 25, except that the reaction time was of 16 h and that ethyl acetate/methanol (9:1) was used. Yield: 47%; MS: m/z=506 (M+H).

Example 46

1-[6-(3-Dimethylamino-pyrrolidin-1-yl)-4-(4-fluoro-phenyl)-2-methyl-quinolin-3-yl]-2,2,2-trifluoro-ethanone The title compound was prepared from 1-[6-Bromo-4-(4-fluoro-phenyl)-2-methyl-quinolin-3-yl]-2,2,2-trifluoro-ethanone [example 24] and 3-(dimethylamino)pyrrolidine according to the procedure of example 25, except that the reaction time was of 16 h and that ethyl acetate/methanol (9:1) was used. Yield: 44%; MS: m/z=446 (M+H).

Example 47

2,2,2-Trifluoro-1-[6-iodo-4-(4-methanesulfonyl-phenyl)-2-methyl-quinolin-3-yl]-ethanone The title compound was prepared from (2-Amino-5-iodo-phenyl)-(4-methanesulfonyl-phenyl)-methanone [example A17] and 1,1,1-trifluoro-2,4-pentanedione according to the procedure of example 1, except that the solvent was isopropanol, the reaction time was of 16 h and heptane/ethyl acetate (1:2) was used. Yield: 55%; MS: m/z=519 (M).

Example 48

2,2,2-Trifluoro-1-[6-(4-hydroxy-4-methyl-piperidin-1-yl)-4-(4-methanesulfonyl-phenyl)-2-methyl-quinolin-3-yl]-ethanone The title compound was prepared from 1-[6-bromo-4-(4-methanesulfonyl-phenyl)-2-methyl-quinolin-3-yl]-2,2,2-trifluoro-ethanone [example 23] and 4-methyl-piperidin-4-ol according to the procedure of example 25. Yield: 14%; MS: m/z=507 (M+H).

Example 49

2,2,2-Trifluoro-1-[4-(4-methanesulfonyl-phenyl)-6-(4-methoxy-piperidin-1-yl)-2-methyl-quinolin-3-yl]-ethanone The title compound was prepared from 1-[6-bromo-4-(4-methanesulfonyl-phenyl)-2-methyl-quinolin-3-yl]-2,2,2-trifluoro-ethanone [example 23] and 4-methoxy-piperidine according to the procedure of example 25. Yield: 14%; MS: m/z=507 (M+H).

Example 50

[6-Bromo-4-(4-methanesulfonyl-phenyl)-2-methyl-quinolin-3-yl]-cyclopropyl-methanone The title compound was prepared from (2-Amino-5-bromo-phenyl)-(4-methanesulfonyl-phenyl)-methanone [example A15] and 1-cyclopropyl-1,3-butanedione according to the procedure of example 1, except that the solvent was isopropanol, the reaction time was of 16 h and heptane/ethyl acetate (1:2) was used. Yield: 47%; MS: m/z=443 (M+H).

Example 51

Cyclopropyl-[4-(4-methanesulfonyl-phenyl)-2-methyl-6-morpholin-4-yl-quinolin-3-yl]-methanone A tube placed under argon was charged with tris(dibenzylideneacetone)dipalladium chloroform complex (5 mg), 2-dicyclohexylphosphino-2',4',6'-triisopropylbiphenyl (5 mg) and cesium carbonate (110 mg, 0.33 mmol). [6-Bromo-4-(4-methanesulfonyl-phenyl)-2-methyl-quinolin-3-yl]-cyclopropyl-methanone [example 50] (100 mg, 0.22 mmol) in t-BuOH (5 ml) was added, followed by morpholine (24 mg, 0.27 mmol). The tube was sealed and heated at 110° C. for 6 hrs. The reaction mixture was cooled to 20° C., diluted with heptane, and filtered through Celite and purified directly by flash chromatography on silica gel in heptane/AcOEt 80:20 to give a yellow solid (52 mg, 51%). MS: m/z=451 (M+H).

Example 52

1-[6-(3,3-Difluoro-piperidin-1-yl)-4-(4-methanesulfonyl-phenyl)-2-methyl-quinolin-3-yl]-2,2,2-trifluoro-ethanone The title compound was prepared from 1-[6-Bromo-4-(4-methanesulfonyl-phenyl)-2-methyl-quinolin-3-yl]-2,2,2-trifluoro-ethanone [example 23] and 3,3-difluoropiperidine hydrochloride according to the procedure of example 51. Yield: 50%; MS: m/z=. 513 (M+H).

Example 53

2,2,2-Trifluoro-1-[4-(4-methanesulfonyl-phenyl)-2-methyl-6-(8-oxa-3-aza-bicyclo[3.2.1]oct-3-yl)-quinolin-3-yl]-ethanone The title compound was prepared from 1-[6-bromo-4-(4-methanesulfonyl-phenyl)-2-methyl-quinolin-3-yl]-2,2,2-trifluoro-ethanone [example 23] and 8-oxa-3-aza-bicyclo[3.2.1]octane according to the procedure of example 51. Yield: 61%; MS: m/z=505 (M+H).

Example 54

Cyclopropyl-[4-(4-methanesulfonyl-phenyl)-2-methyl-6-piperidin-1-yl-quinolin-3-yl]-methanone The title compound was prepared from [6-Bromo-4-(4-methanesulfonyl-phenyl)-2-methyl-quinolin-3-yl]-cyclopropyl-methanone [example 50] and piperidine according to the procedure of example 51. Yield: 39%; MS: m/z=449 (M+H).

Example 55

[(6-Bromo-2-methyl-4-phenyl-quinolin-3-yl)-cyclopropyl-methanone

The title compound was prepared from (2-amino-5-bromo-phenyl)-phenyl-methanone [example A16] and 1-cyclopropyl-1,3-butanedione according to the procedure of example 1, except that the solvent was isopropanol, the reaction time was of 16 h and heptane/ethyl acetate (1:2) was used. Yield: 75%; MS: m/z=366 (M).

Example 56

[6-Bromo-4-(4-fluoro-phenyl)-2-methyl-quinolin-3-yl]-cyclopropyl-methanone

The title compound was prepared from (2-amino-5-trifluoromethoxy-phenyl)-(4-fluorophenyl)-methanone [example A9] and 1-cyclopropyl-1,3-butanedione according to the procedure of example 1, except that the solvent was isopropanol, the reaction time was of 16 h and heptane/ethyl acetate (1:2) was used. Yield: 76%; MS: m/z=384 (M).

Example 57

Cyclopropyl-(2-methyl-4-phenyl-6-piperidin-1-yl-quinolin-3-yl)-methanone

The title compound was prepared from [(6-Bromo-2-methyl-4-phenyl-quinolin-3-yl)-cyclopropyl-methanone [example 55] and piperidine according to the procedure of example 51. Yield: 64%; MS: m/z=371 (M+H).

Example 58

Cyclopropyl-(2-methyl-6-morpholin-4-yl-4-phenyl-quinolin-3-yl)-methanone

The title compound was prepared from [(6-Bromo-2-methyl-4-phenyl-quinolin-3-yl)-cyclopropyl-methanone [example 55] and morpholine according to the procedure of example 51. Yield: 67%; MS: m/z=373 (M+H).

What is claimed is:

1. A compound of formula I

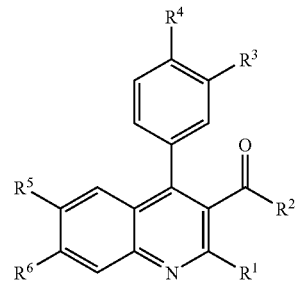

wherein
R$^1$ is hydrogen, C$_1$-C$_7$ alkyl, C$_1$-C$_7$ haloalkyl, di(C$_1$-C$_7$)alkylamino, C$_3$-C$_8$ cycloalkyl, or a 5 or 6 membered heterocycloalkyl;
R$^2$ is C$_1$-C$_7$ alkyl, aryl, C$_1$-C$_7$ alkoxy(C$_1$-C$_7$)alkyl, C$_1$-C$_7$ haloalkyl or C$_3$-C$_8$ cycloalkyl;
R$^3$ and R$^4$ are each independently hydrogen, halo, hydroxy, C$_1$-C$_7$ alkoxy, C$_1$-C$_7$ haloalkoxy, di(C$_1$-C$_7$)alkylamino, C$_1$-C$_7$ alkylsulfonyl, or a 5 or 6 membered heterocycloalkyl;
R$^5$ is aryloxy, or is —NR$^7$R$^8$ wherein R$^7$ and R$^8$ are each independently C$_1$-C$_7$ alkyl, or R$^7$ and R$^8$, together with the nitrogen atom to which they are attached, form 4 to 7 membered heterocycloalkyl group which is optionally substituted by one or more subsituent(s) selected from the group consisting of halo, C$_1$-C$_7$ alkyl, C$_1$-C$_7$ alkoxy, hydroxy, phenyl and di(C$_1$-C$_7$)alkylamino; and
R$^6$ is hydrogen or together with R$^5$ forms a 5 or 6 membered heterocycloalkyl group which is optionally substituted by one or more halogen;
or a pharmaceutically acceptable acid addition salt thereof.

2. A compound of formula I according to claim 1, wherein
R$^1$ is C$_1$-C$_7$ alkyl;
R$^2$ is C$_1$-C$_7$ alkyl, phenyl, or C$_1$-C$_7$ haloalkyl;
R$^3$ and R$^4$ are each independently hydrogen, halo, C$_1$-C$_7$ alkoxy, or C$_1$-C$_7$ alkylsulfonyl;
R$^5$ is, aryloxy, or —NR$^7$R$^8$ wherein R$^7$ and R$^8$ are each independently C$_1$-C$_7$ alkyl, or, together with the nitrogen atom to which they are attached, form or a 4 to 7 membered heterocycloalkyl group which is optionally substituted by one or more subsituent(s) selected from the group consisting of halo, C$_1$-C$_7$ alkyl, hydroxy, C$_1$-C$_7$ alkoxy, phenyl and di(C$_1$-C$_7$)alkylamino; and
R$^6$ is hydrogen or together with R$^5$ forms a 5 or 6 membered heterocycloalkyl group which is optionally substituted by one or more halogen;
or a pharmaceutically acceptable acid addition salt thereof.

3. A compound of claim 1, wherein R$^1$ is C$_1$-C$_7$ alkyl.

4. A compound of claim 3, wherein R$^1$ is selected from the group consisting of methyl, ethyl, propyl, isopropyl, butyl, isobutyl, and t-butyl.

5. A compound of claim 1, wherein R$^2$ is selected from the group consisting of C$_1$-C$_7$ alkyl, aryl, C$_1$-C$_7$ haloalkyl and C$_3$-C$_8$ cycloalkyl.

6. A compound of claim 5, wherein R$^2$ is C$_1$-C$_7$ alkyl.

7. A compound which is:
1-[4-(4-Chloro-phenyl)-2-methyl-6-trifluoromethoxy-quinolin-3-yl]-ethanone;
1-[4-(4-Chloro-phenyl)-2-methyl-6-phenoxy-quinolin-3-yl]-ethanone.

8. A compound of claim 5, wherein $R^2$ is $C_1$-$C_7$ haloalkyl.

9. A compound which is:
  1-(2,2-Difluoro-6-methyl-8-phenyl-[1,3]dioxolo[4,5-g]quinolin-7-yl)-2,2,2-trifluoro-ethanone.

10. A compound of claim 8, selected from the group consisting of:
  2,2,2-Trifluoro-1-(2-methyl-4-phenyl-6-piperidin-1-yl-quinolin-3-yl)-ethanone;
  2,2,2-Trifluoro-1-(2-methyl-6-morpholin-4-yl-4-phenyl-quinolin-3-yl)-ethanone;
  2,2,2-Trifluoro-1-(2-methyl-4-phenyl-6-pyrrolidin-1-yl-quinolin-3-yl)-ethanone;
  2,2,2-Trifluoro-1-[2-methyl-6-(2-methyl-pyrrolidin-1-yl)-4-phenyl-quinolin-3-yl]-ethanone;
  2,2,2-Trifluoro-1-[2-methyl-6-(4-methyl-piperazin-1-yl)-4-phenyl-quinolin-3-yl]-ethanone;
  2,2,2-Trifluoro-1-[6-(3-hydroxy-pyrrolidin-1-yl)-2-methyl-4-phenyl-quinolin-3-yl]-ethanone; and
  2,2,2-Trifluoro-1-[6-(3-hydroxy-azetidin-1-yl)-2-methyl-4-phenyl-quinolin-3-yl]-ethanone.

11. A compound of claim 8, selected from the group consisting of:
  2,2,2-Trifluoro-1-[4-(4-methanesulfonyl-phenyl)-2-methyl-6-piperidin-1-yl-quinolin-3-yl]-ethanone;
  2,2,2-Trifluoro-1-[4-(4-fluoro-phenyl)-2-methyl-6-piperidin-1-yl-quinolin-3-yl]-ethanone;
  2,2,2-Trifluoro-1-[4-(4-fluoro-phenyl)-2-methyl-6-morpholin-4-yl-quinolin-3-yl]-ethanone;
  2,2,2-Trifluoro-1-[4-(4-methanesulfonyl-phenyl)-2-methyl-6-pyrrolidin-1-yl-quinolin-3-yl]-ethanone;
  2,2,2-Trifluoro-1-[4-(4-fluoro-phenyl)-2-methyl-6-pyrrolidin-1-yl-quinolin-3-yl]-ethanone;
  2,2,2-Trifluoro-1-[4-(4-fluoro-phenyl)-6-(3-hydroxy-pyrrolidin-1-yl)-2-methyl-quinolin-3-yl]-ethanone;
  2,2,2-Trifluoro-1-[6-(4-hydroxy-4-phenyl-piperidin-1-yl)-2-methyl-4-phenyl-quinolin-3-yl]-ethanone;
  2,2,2-Trifluoro-1-[6-(4-hydroxy-4-phenyl-piperidin-1-yl)-4-(4-methanesulfonyl-phenyl)-2-methyl-quinolin-3-yl]-ethanone; and
  2,2,2-Trifluoro-1-[4-(4-fluoro-phenyl)-6-(4-hydroxy-4-phenyl-piperidin-1-yl)-2-methyl-quinolin-3-yl]-ethanone.

12. A compound of claim 8, selected from the group consisting of:
  2,2,2-Trifluoro-1-[4-(4-fluoro-phenyl)-6-(3-hydroxy-azetidin-1-yl)-2-methyl-quinolin-3-yl]-ethanone;
  1-[6-Azepan-1-yl-4-(4-fluoro-phenyl)-2-methyl-quinolin-3-yl]-2,2,2-trifluoro-ethanone;
  1-(6-Azepan-1-yl-2-methyl-4-phenyl-quinolin-3-yl)-2,2,2-trifluoro-ethanone;
  1-[6-(3-Dimethylamino-pyrrolidin-1-yl)-2-methyl-4-phenyl-quinolin-3-yl]-2,2,2-trifluoro-ethanone;
  1-[6-(3-Dimethylamino-pyrrolidin-1-yl)-4-(4-methanesulfonyl-phenyl)-2-methyl-quinolin-3-yl]-2,2,2-trifluoro-ethanone;
  1-[6-(3-Dimethylamino-pyrrolidin-1-yl)-4-(4-fluoro-phenyl)-2-methyl-quinolin-3-yl]-2,2,2-trifluoro-ethanone;
  2,2,2-Trifluoro-1-[6-(4-hydroxy-4-methyl-piperidin-1-yl)-4-(4-methanesulfonyl-phenyl)-2-methyl-quinolin-3-yl]-ethanone;
  2,2,2-Trifluoro-1-[4-(4-methanesulfonyl-phenyl)-6-(4-methoxy-piperidin-1-yl)-2-methyl-quinolin-3-yl]-ethanone;
  1-[6-(3,3-Difluoro-piperidin-1-yl)-4-(4-methanesulfonyl-phenyl)-2-methyl-quinolin-3-yl]-2,2,2-trifluoro-ethanone; and
  2,2,2-Trifluoro-1-[4-(4-methanesulfonyl-phenyl)-2-methyl-6-(8-oxa-3-aza-bicyclo[3.2.1]oct-3-yl)-quinolin-3-yl]-ethanone.

13. A compound of claim 5, wherein $R^2$ is cycloalkyl.

14. A compound of claim 13, selected from the group consisting of:
  Cyclopropyl-[4-(4-methanesulfonyl-phenyl)-2-methyl-6-morpholin-4-yl-quinolin-3-yl]-methanone;
  Cyclopropyl-[4-(4-methanesulfonyl-phenyl)-2-methyl-6-piperidin-1-yl-quinolin-3-yl]-methanone;
  Cyclopropyl-(2-methyl-4-phenyl-6-piperidin-1-yl-quinolin-3-yl)-methanone and
  Cyclopropyl-(2-methyl-6-morpholin-4-yl-4-phenyl-quinolin-3-yl)-methanone.

15. A compound of claim 5, wherein $R^2$ is phenyl.

16. A compound of claim 5, wherein $R^2$ is selected from the group consisting of methyl, ethyl, propyl, isopropyl, butyl, isobutyl, cyclopropyl, cyclobutyl, cyclopentyl, cyclohexyl, phenyl, $CHF_2$, and $CF_3$.

17. A compound of claim 1, wherein $R^3$ is hydrogen or halogen.

18. A compound of claim 17, wherein $R^3$ is hydrogen, Cl, or F.

19. A compound of claim 1, wherein $R^4$ is hydrogen, halogen, $C_1$-$C_7$ alkoxy, or $C_1$-$C_7$ alkylsulfonyl.

20. A compound of claim 19, wherein $R^4$ is hydrogen, methoxy, Cl, F or methylsulfonyl.

21. A compound of claim 1, wherein $R^5$ is, aryloxy, or $-NR^7R^8$ wherein $R^7$ and $R^8$, together with the nitrogen atom to which they are attached, form or a 4 to 7 membered heterocycloalkyl group which is optionally substituted by one or more subsituent(s) selected from the group consisting of halo, $C_1$-$C_7$ alkyl, $C_1$-$C_7$ alkoxy, hydroxy, phenyl and di($C_1$-$C_7$) alkylamino.

22. A compound of claim 21, wherein $R^5$ is, PhO, or $-NR^7R^8$, wherein $R^7$ and $R^8$ together with the nitrogen atom to which they are attached form a group selected from the group consisting of piperidin-1-yl, morpholin-4-yl, pyrrolidin-1-yl, piperazin-1-yl, pyrrolidin-1-yl, azetidine-1-yl, and azepan-1-yl, which may be substituted by one or more F, methyl, ethyl, propyl, i-propyl, butyl, i-butyl, t-butyl, hydroxy, methoxy, phenyl, dimethylamino and 1,4-oxazepane and 8-oxa-3-aza-bicyclo[3.2.1]oct-3-yl.

23. A compound of claim 21, wherein $R^5$ is, PhO, or $-NR^7R^8$, wherein $R^7$ and $R^8$ together with the nitrogen atom to which they are attached form a group selected from the group consisting of piperidin-1-yl, 3,3-difluoro-piperidin-1-yl, 4-hydroxy-4-methyl-piperidin-1-yl, 4-methoxy-piperidine-1-yl, morpholin-4-yl, pyrrolidin-1-yl, 2-methyl-pyrrolidin-1-yl, 4-methyl-piperazin-1-yl, 3-hydroxy-pyrrolidin-1-yl, 3-hydroxy-azetidine-1-yl, 4-hydroxy-4phenyl-piperidin-1-yl, 3,3-dimethylamine-pyrrolidin-1-yl, azepan-1-yl and 1,4-oxazepane and 8-oxa-3-aza-bicyclo[3.2.1]oct-3-yl.

24. A pharmaceutical composition comprising a therapeutically effective amount of a compound of formula I

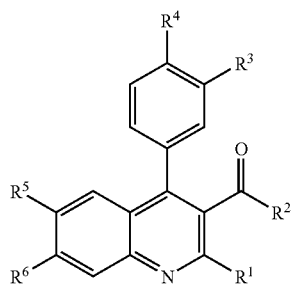

(I)

wherein $R^1$ is hydrogen, $C_1$-$C_7$ alkyl, $C_1$-$C_7$ haloalkyl, di($C_1$-$C_7$)alkylamino, $C_3$-$C_8$ cycloalkyl, or a 5 or 6 membered heterocycloalkyl;

$R^2$ is $C_1$-$C_7$ alkyl, aryl, $C_1$-$C_7$ alkoxy($C_1$-$C_7$)alkyl, $C_1$-$C_7$ haloalkyl or $C_3$-$C_8$ cycloalkyl;

$R^3$ and $R^4$ are each independently hydrogen, halo, hydroxy, $C_1$-$C_7$ alkoxy, $C_1$-$C_7$ haloalkoxy, di($C_1$-$C_7$)alkylamino, $C_1$-$C_7$ alkylsulfonyl, or a 5 or 6 membered heterocycloalkyl;

$R^5$ is, or aryloxy, or is —$NR^7R^8$ wherein $R^7$ and $R^8$ are each independently $C_1$-$C_7$ alkyl, or $R^7$ and $R^8$, together with the nitrogen atom to which they are attached, form a 4 to 7 membered heterocycloalkyl group which is optionally substituted by one or more subsituent(s) selected from the group consisting of halo, $C_1$-$C_7$ alkyl, $C_1$-$C_7$ alkoxy, hydroxy, phenyl and di($C_1$-$C_7$)alkylamino; and $R^6$ is hydrogen or together with $R^5$ forms a 5 or 6 membered heterocycloalkyl group which is optionally substituted by one or more halogen;

or a pharmaceutically acceptable acid addition salt thereof.

* * * * *

UNITED STATES PATENT AND TRADEMARK OFFICE
CERTIFICATE OF CORRECTION

PATENT NO.        : 7,576,217 B2
APPLICATION NO. : 11/259860
DATED             : August 18, 2009
INVENTOR(S)       : Malherbe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 831 days.

Signed and Sealed this

Seventh Day of September, 2010

David J. Kappos
*Director of the United States Patent and Trademark Office*